(12) United States Patent
Brosseau et al.

(10) Patent No.: US 11,761,960 B2
(45) Date of Patent: Sep. 19, 2023

(54) CD24$^{hi}$CD38$^{hi}$ TRANSITIONAL B CELLS AND CD9 AS NEW BIOMARKER OF LONG-TERM HUMAN LUNG ALLOGRAFT SURVIVAL

(71) Applicants: UNIVERSITE DE NANTES, Nantes (FR); INSTITUT NATIONAL DE LA SANTE ET DE LA RECHERCHE MEDICALE (INSERM), Paris (FR); CHU NANTES, Nantes (FR)

(72) Inventors: Carole Brosseau, Coueron (FR); Maxim Durand, Blacy (FR); Antoine Magnan, Nantes (FR); Sophie Brouard, Suće-sur-Erdre (FR)

(73) Assignees: UNIVERSITE DE NANTES, Nantes (FR); INSTITUT NATIONALE DE LE SANTE ET DE LA RECHERCHE MEDICALE, Paris (FR); CHU NANTES, Nantes (FR)

( * ) Notice: Subject to any disclaimer, the term of this patent is extended or adjusted under 35 U.S.C. 154(b) by 838 days.

(21) Appl. No.: 16/607,762

(22) PCT Filed: Apr. 27, 2018

(86) PCT No.: PCT/EP2018/060924
§ 371 (c)(1),
(2) Date: Oct. 24, 2019

(87) PCT Pub. No.: WO2018/197690
PCT Pub. Date: Nov. 1, 2018

(65) Prior Publication Data
US 2020/0057064 A1 Feb. 20, 2020

(30) Foreign Application Priority Data

Apr. 28, 2017 (EP) .................................... 17305479

(51) Int. Cl.
G01N 33/569 (2006.01)
G01N 33/50 (2006.01)

(52) U.S. Cl.
CPC ... *G01N 33/56966* (2013.01); *G01N 33/5052* (2013.01)

(58) Field of Classification Search
CPC .................... G01N 33/56966; G01N 33/5052
See application file for complete search history.

(56) References Cited

PUBLICATIONS

Bigot et al. Transcriptomic Signature of the CD24 hi CD38hi Transitional B cells Associated With an Immunoregulatory Phenotype in Renal Transplant Recipients. American Journal of Transplantation 16: 3430-3442 (2016).*

(Continued)

*Primary Examiner* — Gailene Gabel
(74) *Attorney, Agent, or Firm* — WCF IP

(57) ABSTRACT

The present invention relates to an in vitro method for determining the risk of occurrence of chronic lung graft dysfunction in a human subject comprising: a) measuring the level of CD9$^+$ B cells in a blood sample of the subject, b) comparing the level of CD9$^+$ B cells measured at step a) with one or more reference values of the level of CD9$^+$ B cells, and c) determining the risk of occurrence of chronic lung graft dysfunction in the said subject from the comparison performed at step b).

4 Claims, 21 Drawing Sheets

(56) References Cited

PUBLICATIONS

Kuzmina et al. Excess of BAFF and distortion of B-cell homeostasis in patients with Excess of BAFF and distortion of B-cell homeostasis in patients with newly diagnosed bronchiolitis obliterans syndrome associated with chronic graft-versus-host disease. Bone Marrow Transplantation 46: Suppl.1 Abstract (Apr. 2011).*

Braza et al. A regulatory CD9+ B-cell subset inhibits HDM-induced allergic airway inflammation. European Journal of Allergy and Clinical Immunology. 70: 1421-1431 (Jul. 14, 2015).*

Kuzmina, Z. et al., "CD19+CD21low B cells and patients at risk for NIH-defined chronic graft-versus-host disease with bronchiolitis obliterans syndrome", Blood 121, No. 10, 2013.

* cited by examiner

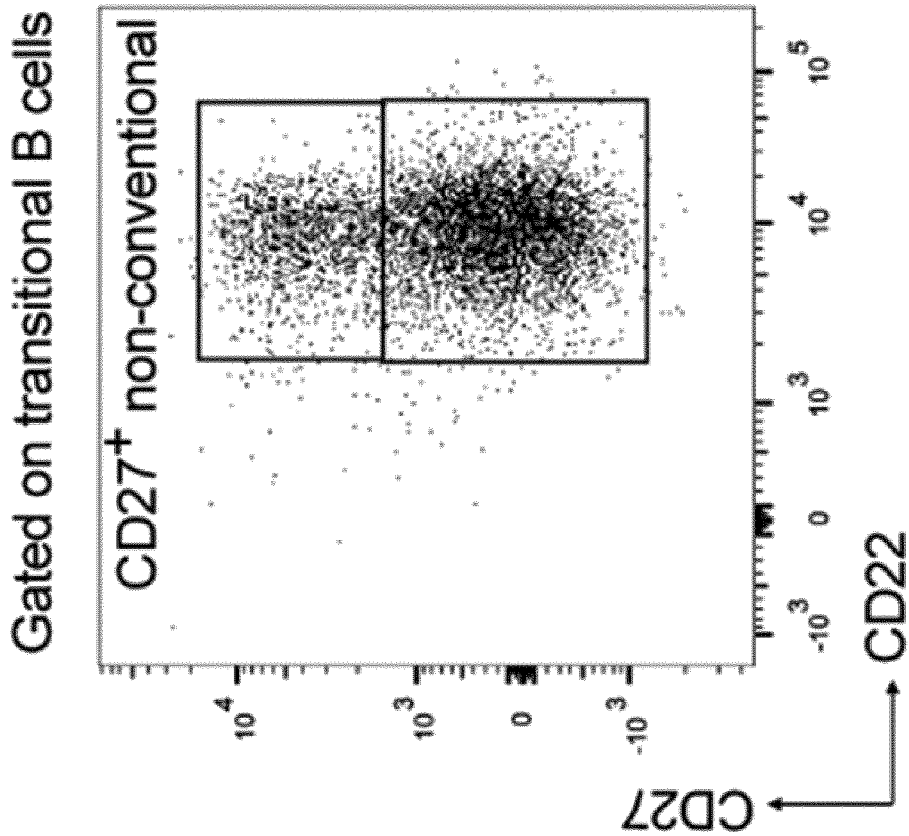
Figure 2A (Continued 1)

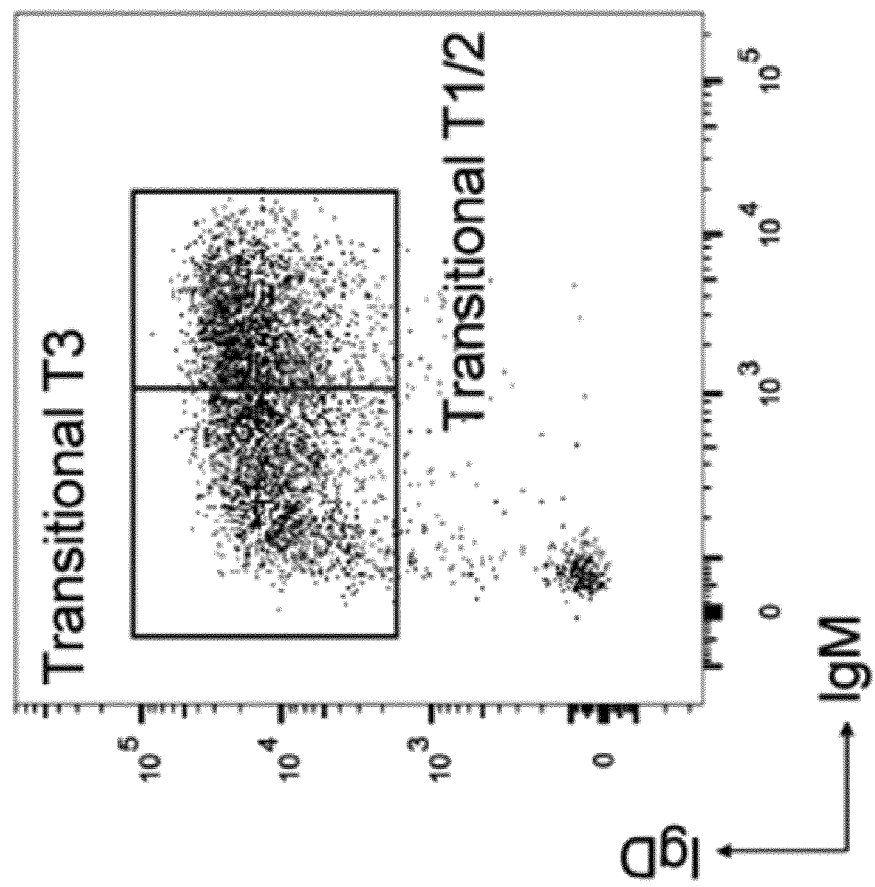
Figure 2A (Continued 2)

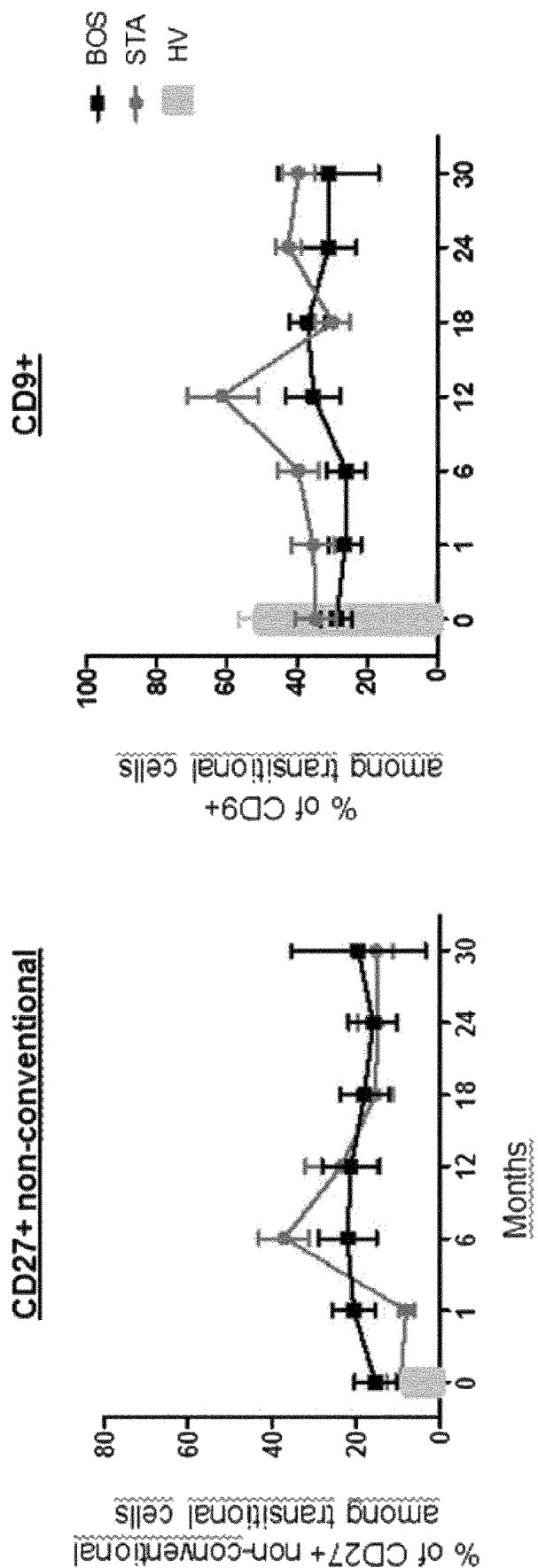
Figure 2B (Continued 1)

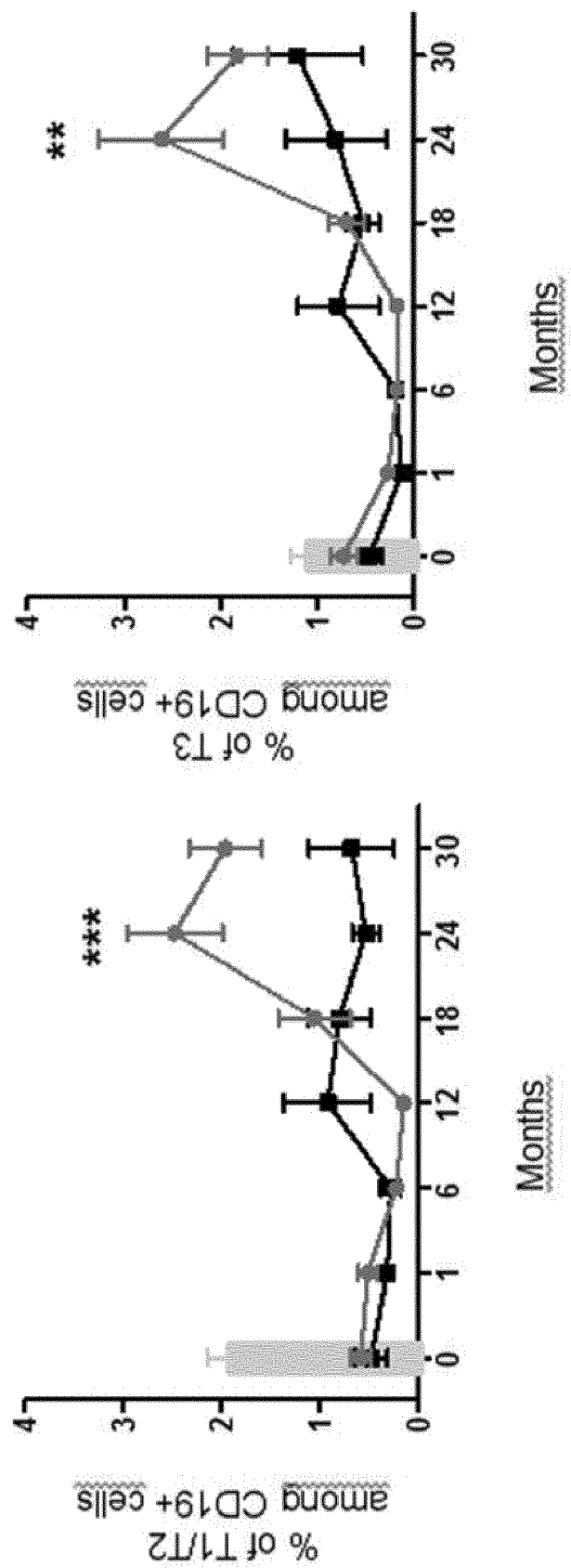
Figure 2B (Continued 2)

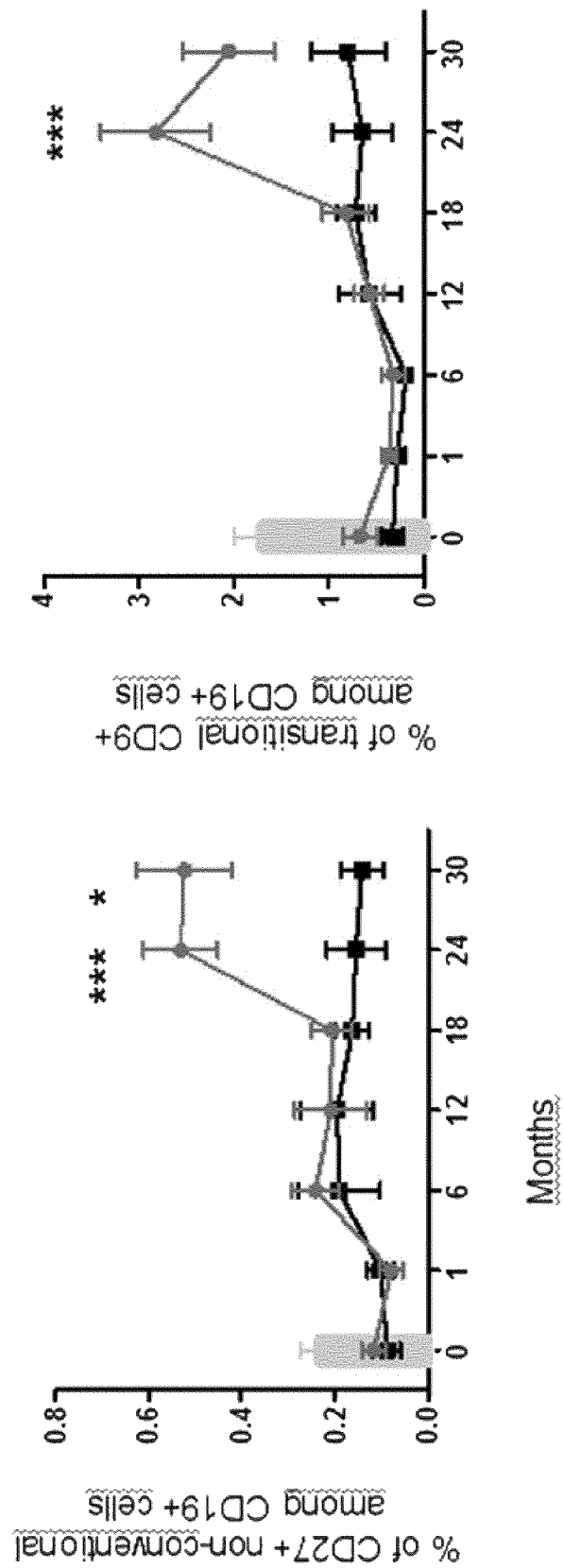
Figure 2B (Continued 3)

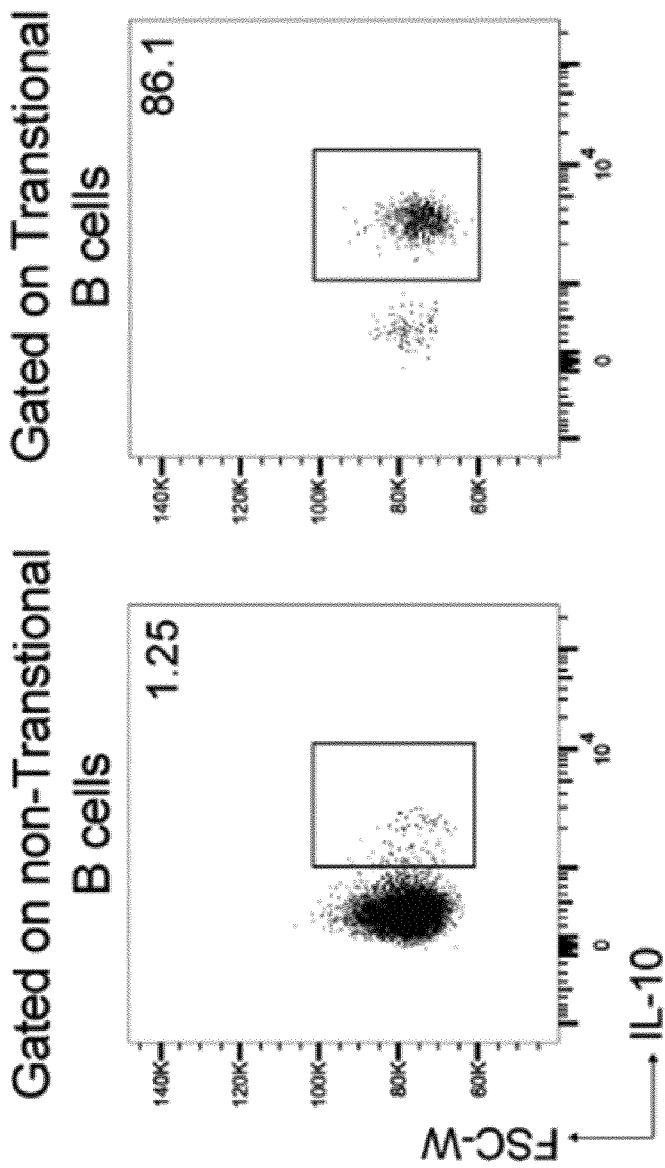
Figure 3B (Continued 1)

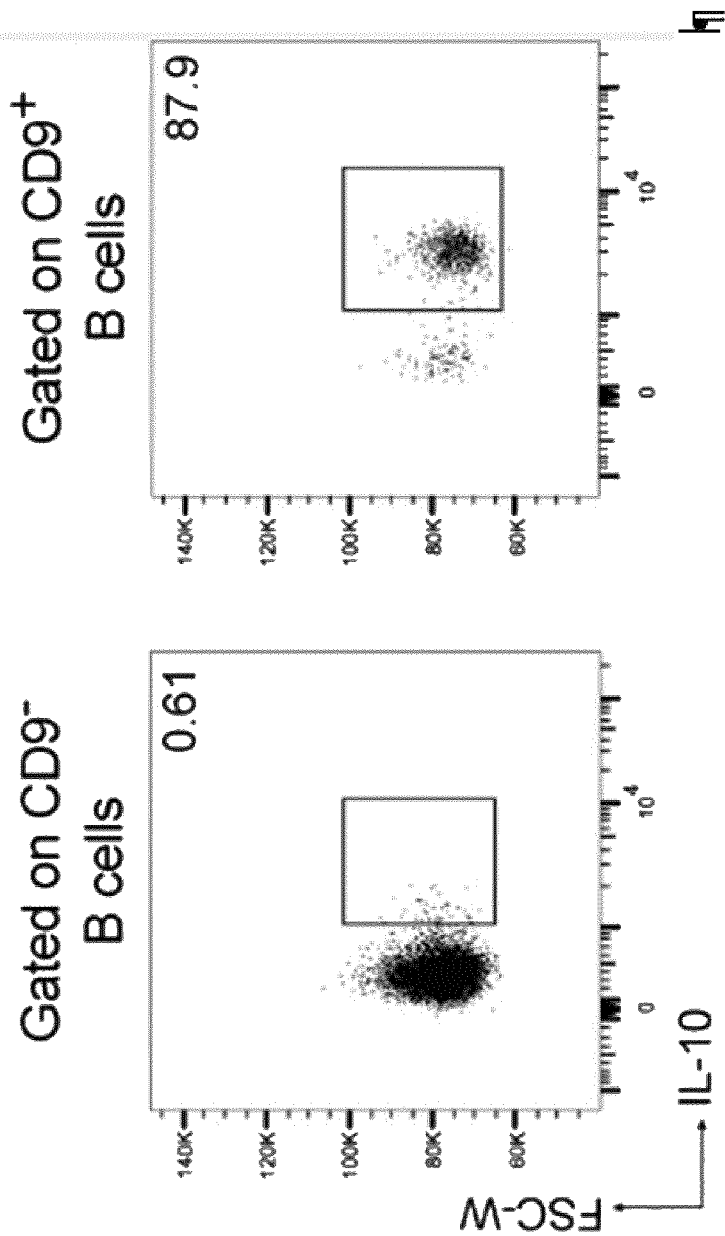
Figure 3B (Continued 2)

# CD24<sup>hi</sup>CD38<sup>hi</sup> TRANSITIONAL B CELLS AND CD9 AS NEW BIOMARKER OF LONG-TERM HUMAN LUNG ALLOGRAFT SURVIVAL

FIELD OF THE INVENTION

This invention lies in the field of prediction of the outcome of an allograft in human, and more precisely relates to markers that are predictive of the outcome of lung allograft in human.

BACKGROUND OF THE INVENTION

Lung transplantation (LT) is the ultimate treatment option for selected patients suffering from end-stage pulmonary diseases. Chronic lung allograft dysfunction (CLAD) is preliminary responsible for the poor long-term outcome of LT with an occurrence of approximately 50% within 5 years (1). The most prevalent morphological feature in CLAD is Bronchiolitis Obliterans Syndrome (BOS) (2-3), defined as an obstructive pulmonary function defect in the absence of other identifiable causes, mostly not amenable to treatment (4). Thus, clinical surrogates used to define BOS are not able to detect early stages of the pathology. The recognition of damages and therefore the diagnosis prior to their development is necessary in designing therapies for BOS prevention. Hence, need to highlight biomarkers for early diagnosis is essential. In this context, several studies have been carried out to identify early indicators of CLAD such as lung biopsy profiling (5), BAL composition, neutrophilia (6,7), cytokines (8), blood level of endothelin-1 (9), plasma level of soluble CD59 (10), HLA-G (11) or matrix metalloproteinase (MMP)-9 (48). But none of these studies have demonstrated enough robustness to achieve clinical acceptance, and CLAD stays unpredictable so far.

There is growing evidence that regulatory B cells (Breg) are associated with the prevention of graft rejection in skin (13), hematopoietic stem cells (14), kidney (15) and mouse model of lung transplantation (16). In the particular state of tolerance, kidney transplanted patients present a B cell gene signature (17, 18, 19) and new data suggest that Breg could serve as a biomarker to determine long-term kidney allograft acceptance and tolerance (20). Bregs are thought to mediate their regulatory capacity predominantly via the secretion of IL-10. Although there is no specific cell marker for IL-10 secreting B cells, certain B cell subsets such as CD19$^+$ CD38$^{hi}$CD24$^{hi}$ transitional B cells, CD19$^+$ CD1d$^{hi}$CD5$^+$ or CD19$^+$ CD9$^+$ B cells have been shown to be enriched in IL-10 competent cells (21-24). In particular, CD19$^+$ CD38$^{hi}$CD24$^{hi}$ transitional B cells were described to play a role, not only in maintaining long-term allograft function, but also in promoting allograft tolerance (20, 25, 26).

There remains a need in the art for one or more markers that would be predictive of the outcome of a lung allograft in a human individual, and notably that would be predictive of the risk of occurrence of a chronic lung graft dysfunction, which encompasses the risk of occurrence of a Bronchiolitis Obliterans Syndrome (BOS).

SUMMARY OF THE INVENTION

This invention relates to the use of markers that have been found to be predictive of the risk of occurrence of chronic lung graft dysfunction in human individuals.

This invention pertains to an in vitro method for determining the risk of occurrence of chronic lung graft dysfunction in a human subject comprising:

a) measuring the level of CD9$^+$ B cells in a blood sample of the subject,
b) comparing the level of CD9$^+$ B cells measured at step a) with one or more reference values of the level of CD9$^+$ B cells, and
c) determining the risk of occurrence of chronic lung graft dysfunction in the said subject from the comparison performed at step b).

In some embodiments of the said method, it further comprises measuring the level of CD24$^{hi}$CD38$^{hi}$B cells from the blood sample of the subject.

This invention also concerns a kit for determining the risk of occurrence of chronic lung graft dysfunction in a subject comprising one or more reagents for detecting or quantifying CD9.

In some embodiments of the said kit, it further comprises one or more reagents for detecting or quantifying CD24.

In some embodiments of the said kit, it further comprises one or more reagents for detecting or quantifying CD38.

The present invention further relates to a method for determining a preventive treatment or a therapeutic treatment of chronic lung graft dysfunction in a subject comprising:

a) performing the in vitro method according to any one of claims 1 and 2 in a blood sample of the subject, whereby the risk of occurrence of chronic lung graft dysfunction in the subject is determined, and
b) determining an appropriate preventive or therapeutic treatment.

DESCRIPTION OF THE FIGURES

FIG. 3: IL-10-secreting B cells

DETAILED DESCRIPTION OF THE INVENTION

Figure 1A:
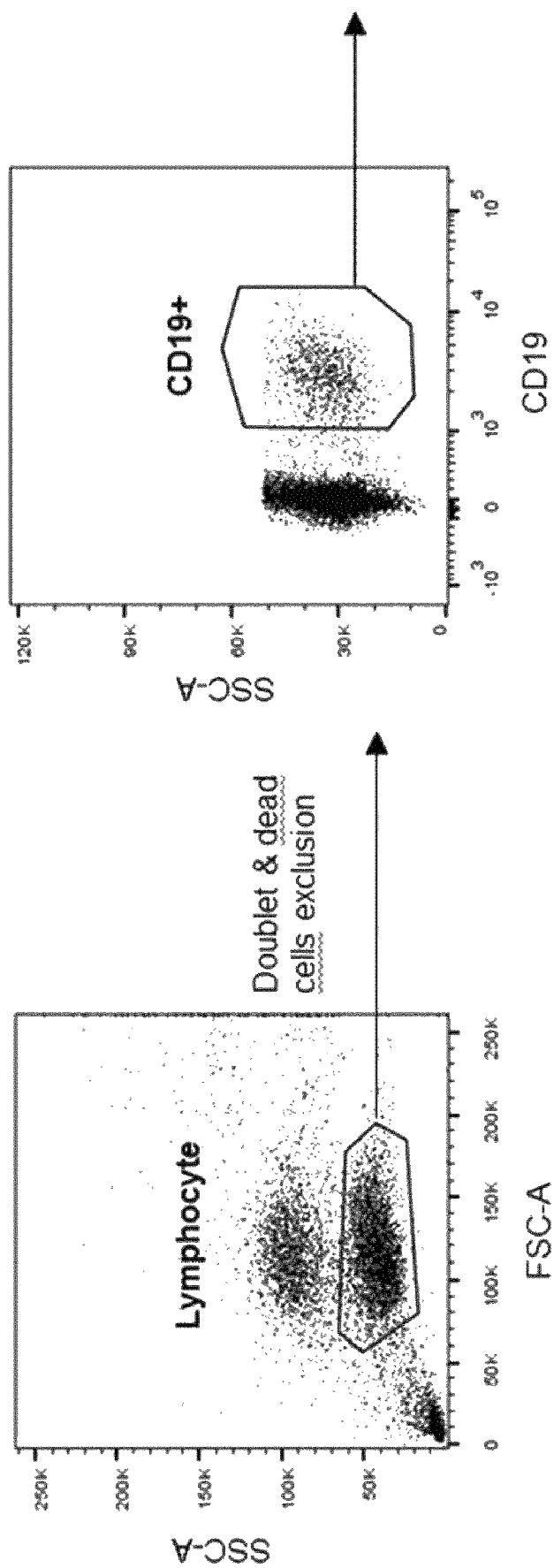
FIG. 1: Longitudinal immunomonitoring of B lymphocyte subpopulations during time. A) Gating strategy of CD19$^+$ B lymphocyte, CD19$^+$ CD27$^+$ memory cells, CD19$^+$ CD27$^-$ naïve cells, CD19$^+$ CD24$^{hi}$CD38$^{hi}$ transitional cells and CD19$^+$ CD24$^-$ CD38$^+$ plasma cells. B) Longitudinal immunomonitoring of CD19$^+$ B cells, transitional, memory, naïve and plasma cells before LT, 1, 6, 12, 18, 24 and 30 months post-LT in STA (n=20), BOS (n=21) and HV (n=20) patients. C) Correlation between the percentage of transitional cells and age, forced inspiratory volume in 1 s (FEV1), and immunosuppressive treatments (***=p<0.001).
Figure 1A:
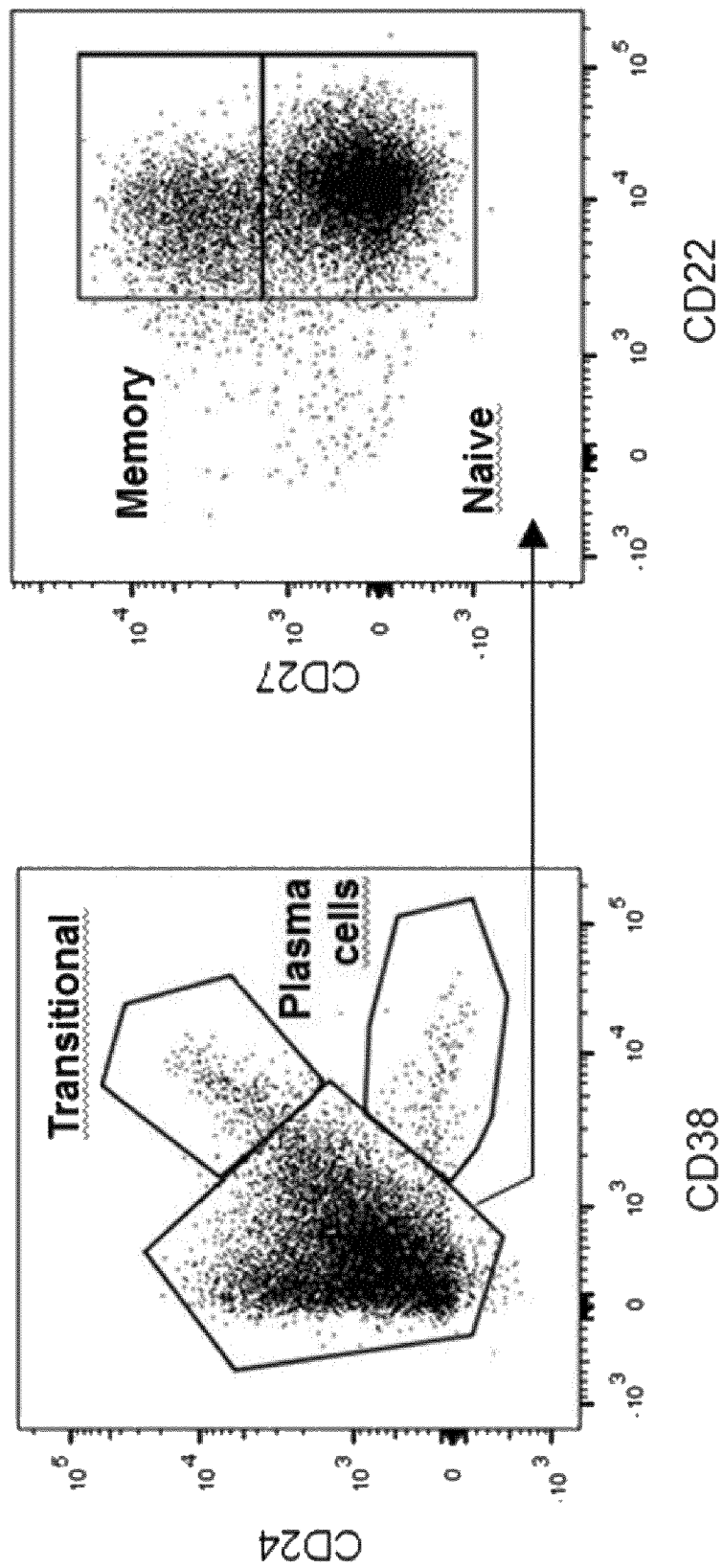

The present inventors aimed to decipher B lymphocyte sub-populations in stable (STA) and Bronchiolitis Obliterans Syndrome (BOS) patients. The present inventors aimed to identify a potential B lymphocyte signature predictive of BOS.

To this end, blood samples from lung transplant patients with stable graft function or with BOS were immune-monitored in a longitudinal way to analyze the homeostasis modifications in the different B cell subsets after transplantation. This study is important at two levels: it is the first reporting on higher level of transitional B cells in patients with stable graft function in lung transplantation and it is reported in the examples herein on CD9+ as a predictive biomarker of BOS. PBMCs from the Lung Transplanted patients (COLT) COhort were immunophenotyped before LT, 1, 6, 12, 18, 24 and 30 months post-LT. PBMCs from patients with long-term functional stability (STA) and healthy volunteers (HV) were analyzed as controls. Cells were stained for the B-cell markers CD19, CD27, CD38, CD138, CD22, CD24, IgD, IgM, CD5 and CD9 to determine the percentage of transitional, naive, plasmablast, memory and regulatory B-cells.

No significant difference was found at the different time points for the number of CD19+B lymphocytes, memory, naive, or plasma cells between BOS and STA patients except for $CD24^{hi}CD38^{hi}$ transitional B cells that stayed low during time in BOS patients (1.1%±0.1) whereas increasing in STA to reach a maximum peak at 24 month (6.3%±0.1; p≤0.001) superior to HV (3.3%±0.4; p≤0.01). These transitional CD9 regulatory markers and secrete IL-10+. Both the level of transitional and its associated marker CD9 were directly associated with long-term BOS-free survival 24 months post-LT. These data show that a low level of $CD24^{hi}CD38^{hi}$ transitional B cells with a regulatory phenotype is associated with a poor grant survival of 5 years post-transplantation. Such newly identified biomarkers now allow early recognition and specific intervention in patients at risk of CLAD and undoubtedly allow improving outcomes, notably by providing means to adapt and monitor preventive treatment as well as therapeutic treatment.

Thus, the inventors have determined a B lymphocyte signature predictive of BOS-free long-term outcomes. As shown in the examples herein, persistent low level of $CD24^{hi}CD38^{hi}$ transitional B cells post-transplantation is associated with BOS development. Conversely, patients able to restore their level of $CD24^{hi}CD38^{hi}$ transitional B cells are more prone to maintain stable graft functions. The results depicted in the examples show that the $CD24^{hi}CD38^{hi}$ transitional B cells and its associated marker CD9, as convincing predictive markers for allograft loss.

Measuring CD9, possibly in combination with $CD24^{hi}CD38^{hi}$, now allows (i) first, early recognition and specific intervention in patients at risk of BOS and (ii) second, identification of patients with low risk of chronic dysfunction to manage treatments administration and reduce their deleterious effects.

Collectively, the inventors' results show that the monitoring of the level of CD9+ B cells is also useful in the early stratification of patients into low and high risk of chronic lung graft dysfunction (CLAD), which encompasses Bronchiolitis Obliterans Syndrome (BOS).

The present inventors have shown that the level of CD9+ B cells is a marker that is indicative of the risk of occurrence of a chronic lung graft dysfunction in a human individual bearing a lung allograft.

Notably, the inventors have shown that that the level of CD9+ B cells is a marker that is indicative of a long-term BOS-free survival of human transplanted with a lung allograft.

The inventors have also shown that the level of $CD24^{hi}CD38^{hi}$ B cells is a marker predictive of the lung allograft outcome.

Thus, the invention relates to the quantification of specific markers at the surface of B cells within a biological sample, as well as to the quantification of B cells expressing these markers within the said biological samples.

Without wishing to be bound by any particular theory, the inventors believe that the level of the said B cells expressing these markers may denote a positive effect of the transitional B cells regarding the lung graft survival. Further, the inventors believe that the same potential mechanisms are induced in any situation involving the presence of an allograft in a human body, which encompasses kidney allograft, skin allograft and hematopoietic cells allograft. Consequently, without wishing to be bound by any particular theory, the inventors believe that the methods disclosed herein which relate to lung allograft shell be extended to any situation of an allografting in a human individual including kidney allograft, skin allograft and hematopoietic cells allograft.

In some embodiments, the level of CD9+ B cells may be used as the sole predictive marker of the occurrence of a chronic lung graft dysfunction, or of the risk of the occurrence of a chronic lung graft dysfunction, since the examples herein have shown that this predictive marker is a highly robust indicator when used alone.

In other embodiments, the marker consisting of the level of CD9+ B cells may be used in combination with one or more further markers indicative of the occurrence of a chronic lung graft dysfunction, or of the risk of the occurrence of a chronic lung graft dysfunction, such as the level of $CD24^{hi}$ $CD38^{hi}$ B cells.

This invention provides an in vitro method for determining the risk of occurrence of chronic lung graft dysfunction in a subject comprising:
  a) measuring the level of CD9+ B cells in a blood sample of the subject,
  b) comparing the level of CD9+ B cells measured at step a) with one or more reference values of the level of CD9+ B cells, and
  c) determining the risk of occurrence of chronic lung graft dysfunction in the said subject from the comparison performed at step b).

According to the invention, a "blood sample" is a biological sample which may encompass any blood sample, or derivative of a blood sample which comprises or which may comprise B cells.

A blood sample may be either a whole blood sample, or a sample which has been obtained after a step of fractionation.

In some embodiments of the said method, the quantification of the said markers is performed on a whole blood sample.

In some other embodiments of the said method, the quantification of markers is performed on a sample selected from the group consisting of (i) purified blood leukocytes, (ii) peripheral blood mononuclear cells or PBMC, (iii) purified lymphocytes, or (iv) purified B cells.

According to an exemplary embodiment, the blood sample may be a sample consisting of peripheral blood mononuclear cells (PBMC).

As used herein, a "subject" encompasses subjects that were grafted with one or two syngeneic or non syngeneic lung(s), including allogenic or even xenogenic, lung(s). Said lung transplanted subject may further have been grafted with another organ of the same donor providing the lung, or a different donor.

In particular, the subject presents a well-functioning lung graft and is under immunosuppressive treatment.

As used herein, a chronic lung allograft dysfunction (CLAD) encompasses a Bronchiolitis Obliterans Syndrome (BOS).

Chronic lung graft dysfunction encompasses graft dysfunction due to chronic antibody mediated and/or cell-mediated rejection of a subject to his graft. Graft dysfunction may be assessed on the basis of a persistent decrease in FEV1 of at least 20% compared with the mean of the two best postoperative values in the absence of any other identifiable cause. The group of patients studied is composed of lung recipients under standard immunosuppression with stable graft function or displaying a bronchiolitis obliterans syndrome.

This invention provides an in vitro method for determining the risk of occurrence of chronic lung graft dysfunction in a subject comprising:
  a) measuring the level of $CD9^+$ B cells in a blood sample of the subject,
  b) comparing the level of $CD9^+$ B cells measured at step a) with one or more reference values of the level of $CD9^+$ B cells, and
  c) determining the risk of occurrence of chronic lung graft dysfunction in the said subject from the comparison performed at step b).

In some embodiments of the in vitro method above, the said method further comprises measuring the level of $CD24^{hi}CD38^{hi}$ B cells from the blood sample of the subject.

The present invention also relates to an in vitro method for determining the risk of occurrence of chronic lung graft dysfunction in a human subject comprising:
  a) measuring the level of $CD24^{hi}CD38^{hi}$ B cells in a blood sample of the subject,
  b) comparing the level of $CD24^{hi}CD38^{hi}$ B cells measured at step a) with one or more reference values of the level of $CD24^{hi}CD38^{hi}$ B cells, and
  c) determining the risk of occurrence of chronic lung graft dysfunction in the said subject from the comparison performed at step b).

In some embodiments, the level of $CD24^{hi}CD38^{hi}$ B cells may be used as the sole predictive marker of the occurrence of a chronic lung graft dysfunction, or of the likelihood of the occurrence of a chronic lung graft dysfunction, since the examples herein have shown that this predictive marker is highly indicative when used alone.

In other embodiments, the marker consisting of the level of $CD24^{hi}CD38^{hi}$ B cells may be used in combination with one or more further markers indicative of the occurrence of a chronic lung graft dysfunction, or of the likelihood of the occurrence of a chronic lung graft dysfunction, such as the level of CD9+ B cells.

Thus, in some embodiments of the in vitro method above, the said method further comprises measuring the level of $CD9^+$ B cells from the blood sample of the subject.

The term "immunosuppressive treatment" refers to the administration to the subject of immunosuppressive drugs or immunosuppressive agents or antirejection medications that inhibit or prevent activity of the immune system. They are used to prevent the rejection of transplanted organs. Biotherapies such as antibody-based therapies are often used.

In the present specification, the name of each of the various markers of interest refers to the internationally recognized name of the corresponding gene, as found in internationally recognized gene sequences and protein sequences databases, including the database from the HUGO Gene Nomenclature Committee, that is available notably at the following Internet address http://www.gene-names.org/.

In the present specification, the name of each of the markers of interest among CD9, CD24 and CD38 may also refer to the internationally recognized name of the corresponding gene, as found in the internationally recognized gene sequences and protein sequences database Genbank.

As used herein, CD9, which may also be termed "cluster of differentiation 9", which is/are encoded respectively by the CD9 gene. CD9 is a member of the transmembrane 4 superfamily, also known as the tetraspanin family.

As used herein, CD24, which may also be termed "cluster of differentiation 24" or "heat stable antigen 24" refers to a protein that in human is a cell adhesion molecule.

As used herein, "$CD24^{hi}$" designates B cells that express the CD24 marker at a high expression level, as it is well known form the one skilled in the art. When referring to $CD24^{hi}$ as a parameter of CD24 protein expression at the surface of B cells, it is admitted in the art that a B cell may be classified as $CD24^{hi}$ when the expression level of CD24 by the said B cell is higher than $10^4$ Fluorescence Units, as determined by FACS analysis, such as illustrated in the examples herein.

As used herein, CD38, which may also be termed "cluster of differentiation 38", which is also known as "cyclic ADP ribose hydrolase" refers to the protein which is encoded by the CD38 gene. When referring to $CD38^{hi}$ as a parameter of CD38 protein expression at the surface of B cells, it is admitted in the art that a B cell may be classified as $CD38^{hi}$ when the expression level of CD38 by the said B cell is higher than $10^4$ Fluorescence Units, as determined by FACS analysis, such as illustrated in the examples herein.

According to the invention, "measuring the level of either one of the markers of the invention" comprises measuring the gene expression level of the marker at a nucleic acid and/or protein level, and preferably at a protein level.

Measuring the gene expression level may thus comprise or consist in (i) measuring the level of expression of a nucleic acid encoding for either one of the markers of the invention, and/or (ii) measuring the level of expression of a protein which is encoded by its corresponding gene.

According to a preferred embodiment, measuring the level of either one of the markers of the invention means measuring the expression of said markers at the surface of B cells. Alternatively, measuring the level of either one of the markers of the invention means measuring the expression of said markers within B cells.

Even more preferably, measuring the level of expression of a marker at the surface of B cells is achieved using flow cytometry, such as Fluorescence Activated Cell Sorting or FACS.

Alternatively, measuring the expression of a marker within B cells can also be achieved by using flow cytometry, in particular by using FACS.

FACS method is well known in the Art and can be achieved as shown in the examples herein. Of course, the one skilled in the art will readily be able to adapt the method depending on the set of markers of which the level needs to be measured.

Step a) of the in vitro method for determining the risk of occurrence of chronic lung graft dysfunction in a subject is preferably performed by measuring a selected marker or a combination of selected markers at the protein level. Most preferably, step a) of the in vitro method for determining the risk of occurrence of chronic lung graft dysfunction in a subject is preferably performed by cytometry, including preferably cytofluorometry (FACS), since cytofluorometry allows measuring the simultaneous presence of the combination of protein markers on the same cell, and thus allows the most precise cell phenotype determination.

In particular, markers of interest according to the present invention which are susceptible to be expressed at the surface of B cells include CD9, CD24 and CD38.

Advantageously, an in vitro method for determining the risk of occurrence of chronic lung graft dysfunction in a subject that includes a step of measuring the level of CD9+ B cells may further comprise a step of measuring the level of one or more additional markers selected in a group comprising $CD24^{hi}$ and $CD38^{hi}$, from a blood sample of a subject.

Advantageously, an in vitro method for determining the risk of occurrence of chronic lung graft dysfunction in a subject that includes a step of measuring the level of $CD24^{hi}CD38^{hi}$ B cells may further comprise a step of measuring the level of the additional marker CD9, from a blood sample of a subject.

The presence or absence of a given marker in the blood sample of a subject is summarized using a well-known terminology in the art. Thus, when a given marker is detected, its corresponding name is followed by a "+" sign, such as in CD9+ or $CD9^+$. Alternatively, when a given marker is not detected, its corresponding name is followed by a "−" sign, such as in CD9− or $CD9^-$.

Of course, the threshold for which a given marker can be detected depends on the technique used for detection. Such a threshold may for instance be determined by the ability of a given ligand (i.e. an antibody) to fix the said marker.

In FACS, a population of cells expressing the said marker can be readily distinguished from a population of cells not expressing the said marker, within the same sample or with distinct samples for establishing a reference.

Also, in FACS, a population of cells expressing a high level of the said marker can be readily distinguished from a population of cells expressing a low level or alternatively not expressing the said marker, within the same sample or with distinct samples for establishing a reference.

Alternatively, a given marker may be expressed at different levels. Such a case may for instance be observed for $CD24^{hi}$ and $CD38^{hi}$.

Accordingly, when such a case occurs, it is preferable to consider only a B cell population with the highest level of expression, or in that case $CD24^{hi}$ and $CD38^{hi}$, which may thus be also referred respectively as CD24+ and CD38+ herein.

Of course, either one of the in vitro methods for determining the risk of occurrence of chronic lung graft dysfunction in a subject is suitable for the invention, and can be readily applied to a method for preventing chronic lung graft dysfunction in a subject.

As it has been mentioned elsewhere in the present specification, the in vitro prediction method described herein, because it allows prognosis of the risk of occurrence of a chronic lung graft dysfunction, or also allows prognosis of the severity of the predicted chronic lung graft dysfunction, also allows the monitoring of the grafted human individuals, so as to prevent the occurrence of chronic lung graft dysfunction or to adapt a therapeutic treatment of a chronic lung graft dysfunction.

Thus, according to another embodiment, the invention relates to a method for determining a preventive or a therapeutic treatment of chronic lung graft dysfunction in a subject comprising:
  a) performing the in vitro method as defined previously, in a blood sample of the subject, whereby the risk of occurrence of chronic lung graft dysfunction in the subject is determined, and
  b) determining an appropriate preventive or therapeutic treatment.

Indeed, step b) of the above method consists for the skilled in the art of intellectually conceiving the said preventive or therapeutic treatment and does not comprises a step of administering the said preventive treatment or the said therapeutic treatment to the said subject.

In some embodiments of the above method, step b) of the said method consists for the skilled in the art of intellectually conceiving and materially preparing the ingredients that shall contain the said preventive or therapeutic treatment and does not comprises a step of administering the said preventive treatment or the said therapeutic treatment to the said subject.

According to still another embodiment, the invention relates to a method for preventing chronic lung graft dysfunction in a subject comprising:
  a) performing the in vitro method as defined previously, in a blood sample of the subject, whereby the risk of occurrence of chronic lung graft dysfunction in the subject is determined, and
  b) administering to the subject a suitable therapeutic treatment.

The "subject" is in particular a lung recipient with current stable graft function, optionally under immunosuppressive treatment.

A suitable therapeutic treatment may be any method known in the art to be useful for preventing chronic lung graft dysfunction, such as an immunosuppressive treatment. Alternatively, the administration to the subject of a suitable therapeutic treatment may replace and/or adapt another pre-established treatment.

The adaptation of the immunosuppressive treatment may consist in: a modification of said immunosuppressive treatment if the subject has been determined as having a risk of occurrence of a chronic lung graft dysfunction, which includes that the subject is "at risk" of developing a graft rejection, or a maintenance or a diminution of said immunosuppressive treatment if the subject has been determined as having a low risk or no risk of occurrence of a chronic lung graft dysfunction, which includes that the subject has a low risk or has no risk of developing a graft rejection.

The present invention presents a major interest. It permits to diagnose or prognose (i.e. to identify), among patients under immunosuppressive treatment, those who are in the process of rejecting their graft and who could thus benefit from an adapted immunosuppressive treatment dedicated to stop or at least slow down the rejection process. Due to the non-reversible aspects of the damages caused by chronic rejection and the current late diagnosis of such phenotype, this achievement is really crucial and would allow a better management of the patients.

The determination of the presence of a graft rejection or graft non-rejection phenotype is carried out thanks to the comparison of the obtained expression profile with a reference value from at least one reference expression profile in step (b) of an in vitro predictive method described herein.

A reference value is required when only one marker selected in the group consisting of CD9, CD24 and CD38 is measured at step a) of the relevant in vitro prediction method described herein.

A reference expression profile is required when more than one marker selected in the group consisting of CD9, CD24 and CD38 is measured at step a) of the relevant in vitro prediction method described herein, including when all the CD9, CD24 and CD38 markers are measured at step a) of the relevant in vitro prediction method described herein.

A "reference expression profile" is a predetermined expression profile, obtained from a biological sample from a subject with a known particular graft state. In particular embodiments, the reference expression profile used for comparison with the test sample in step (b) may have been obtained from a biological sample from a group of healthy volunteers ("healthy reference expression profile") and/or from a biological sample from a graft rejecting subject ("rejecting reference expression profile"), and/or from a biological sample from a graft non-rejecting subject ("non-rejecting reference expression profile").

A reference expression profile may be determined either from one single subject, or from a panel of subjects with a known particular graft state or from a panel of healthy volunteers with a known well-functioning lung.

For instance, a reference expression profile may be determined from one single reference subject, wherein the reference subject is different from the subject to be tested.

Alternatively, a reference expression profile may be determined from one single reference subject, wherein the reference subject is the same as the subject to be tested, but at a different timeline.

According to such embodiment, the in vitro method for determining the risk of occurrence of chronic lung graft dysfunction in a subject may be used as a mean to follow the evolution of an expression profile over time.

Preferably, at least one reference expression profile is a rejecting reference expression profile (or chronic lung graft rejection). Alternatively, at least one reference expression profile may be a non-rejecting reference expression profile. Alternatively, at least one reference expression profile may be a healthy reference expression profile. More preferably, the determination of the presence or absence of a graft rejection phenotype is carried out by comparison with at least one rejecting and at least one non-rejecting reference expression profiles or healthy reference expression profile. The diagnosis (or prognostic) may thus be performed using one rejecting reference expression profile and one non-rejecting reference expression profile or healthy reference expression profile. Advantageously, to get a stronger diagnosis, said diagnosis is carried out using several rejecting reference expression profiles and several non-rejecting reference expression profiles or several healthy reference expression profiles.

The comparison of a tested subject expression profile with said reference expression profile(s) may be performed using statistical models or machine learning methods which aim is to predict a clinical response based on a combination of the explanatory variables (i.e. expression of markers of the invention) and demographic and clinical parameters (recipient age, donor age, recipient gender, donor gender).

In particular, a gene expression level may be measured at the genomic and/or nucleic and/or protein level, and preferably at a protein level.

Preferably, a "reference expression profile" is determined by measuring the level of expression of more than one markers of the invention at the surface of B cells. Even more preferably, a "reference expression profile" is established using flow cytometry, such as FACS method.

The method according to the invention is dedicated for determining the risk of occurrence of chronic lung graft dysfunction in a subject within a "long term" period, which designates a follow up of the patients after their enrollment in the study until graft rejection Kits for Determining the Risk of Occurrence of Chronic Lung Graft Dysfunction According to another of its objects, the invention relates to a kit for determining the risk of occurrence of chronic lung graft dysfunction in a subject, comprising one or more reagents for detecting or quantifying CD9, CD24 and CD38 level in B cells.

According to a particular embodiment, the invention relates to a kit for determining the risk of occurrence of chronic lung graft dysfunction in a subject, comprising one or more reagents for detecting or quantifying CD9 in B cells.

According to other embodiments, the invention relates to a kit for determining the risk of occurrence of chronic lung graft dysfunction in a subject, comprising one or more reagents for detecting or quantifying CD24 and CD38 in B cells.

According to further embodiments, the invention relates to a kit for determining the risk of occurrence of chronic lung graft dysfunction in a subject, comprising one or more reagents for detecting or quantifying CD9, CD24 and CD38 in B cells.

In particular, a reagent may be an antibody.

References for said antibodies may vary depending on the method used for determining the level of said markers.

Accordingly, when the method for determining the level of said markers is flow cytometry, one may for instance refer to the antibodies which have been described in the examples.

Of course, combinations of said reagents are also considered by the invention, as well as modified reagents. As an example, antibodies which linked covalently or non-covalently to a detectable molecule are also considered.

In addition, other reagents may be included in said kits, such as reagents for staining dead cells, and/or reagents or any other sample, or biological sample, which may be used for the purposes of an internal control, such as a reference blood sample.

Such kit for determining the risk of occurrence of chronic lung graft dysfunction in a subject may also further comprise at least one reagent for determination of at least one additional parameter useful for the detection, such as standard biological parameters specific for said subject grafted organ type (notably the presence of anti-HLA antibodies), phenotypic analyses of peripheral blood cells, and quantitative and/or qualitative analysis of peripheral blood cells immune repertoire.

In some embodiments, such kit further comprises a support containing the values of a "reference expression profile" for the purpose of using the kit for performing an in vitro method for determining the risk of occurrence of chronic lung graft dysfunction in a subject that is described in the present specification. The support containing the values of a "reference expression profile" may be selected in a group of supports comprising an analog technical information support such a printed solid support, or a digital information support such as a digital information storage device, which includes a digital information storage memory, a CD, a DVD, etc.

The present invention is further illustrated by, without in any way being limited to, the examples herein.

EXAMPLES

A. MATERIAL AND METHODS
A.1. Patients and Study Design

The University Hospital Ethical Committee of Nantes and the Committee for the Protection of Patients from Biologic Risks approved this study. All patients who participated in this study gave informed consent. Blood samples were selected from transplant patients included in the multicentric longitudinal cohort COLT (Cohort in Lung Transplantation, NCT00980967). This cohort consists in monitoring patients during 5 years following lung transplantation in order to characterize predictive factors of chronic lung allograft dysfunction. Pulmonary function tests, clinical data and blood samples were collected at the inclusion visit before transplantation, the day of transplantation, 1 month post-transplantation and every six months after transplantation up to 5 years. STA and BOS phenotypes were confirmed by a committee of clinicians and researchers based on the values of the pulmonary function test, computerized tomography and after elimination of confounding factors in line with the charter ISHLT/ERS/ATS (27). In the study, patients included are lung-only transplanted patients, did not develop post transplantation lymphoma disease and were not subject to CMV reactivation after lung TP. Thus, 20 STA patients, 21 BOS patients were selected and 20 healthy volunteers (HV) were also analyzed as control. For each patient, we interested in the visit at the inclusion before LT, 1, 6, 12, 18, 24 and 30 months after transplantation. Demographic feature and clinical data are summarized in table 1.

A.2. Cell Isolation and Flow Cytometry

Peripheral blood mononuclear cells (PBMC) were isolated by Ficoll-Paque (GE Healthcare, Marolles-en-Hurepoix, France) gradient centrifugation, frozen and stored at the Centre de Ressources Biologiques (CRB) of Nantes. PBMC were rapidly thawed by placing cryovials at 37° C., washed and stained according to standard protocols using the following mAbs: CD19-BUV395, CD27-BUV737, CD38-BV605, CD138-APC, CD24-PerCP-Cy5.5, CD9-BV510, CD22-PeCy7, IgD-PE, IgD-FITC (BD Biosciences, Le Pont de Claix, France). Markers were used to distinguish CD19+ B lymphocytes, CD19+CD27+ memory cells, CD19+CD27− naive cells, CD19+CD24hiCD38hi transitional cells, and CD19+CD24−CD38+ plasma cells. Dead cells were excluded using the Zombie NIR Fixable Viability kit (BioLegend, London, UK). Samples were run on a BD LSRFORTESSA X-20 (BD Biosciences, Le Pont de Claix, France), and data were analyzed using FlowJo v10 software (FlowJo LLC, Ashland, Oreg., USA).

For all experiments, dead cells were excluded using the Zombie NIR™ Fixable Viability kit (BioLegend, London, UK).

A.3. Analysis of IL-10 Production by Stimulated B Cells

Cells were stimulated for 5 h with phorbol 12-myristate 13-acetate (PMA) (50 ng/ml), ionomycin (0.5 mg/ml), and brefeldin-A (10 mg/ml) (Sigma-Aldrich, St. Louis, Mo., USA). For detection of intracellular IL-10, cells were fixed and permeabilized using the Permabilization/Fixation Kit (BD Biosciences) and staining was performed using anti-IL-10-PE (BD Biosciences). Unstimulated B cells (without/ionomycin stimulation) were stained and used as a control for the analysis.

A.4. Statistics

Longitudinal analysis between the two groups BOS and STA was performed using two-way ANOVA followed by a Bonferroni post hoc test, Pearson correlation, ROC curves survival analysis with Kaplan-Meier (log-rank test), Student's t-test, or chi-square for qualitative variables in GraphPad Prism v5, (GraphPad Software, La Jolla, Calif., USA) after checking Gaussian distribution with the D'Agostino-Pearson test. A p-value<0.05 was considered to be significant.

Example 1

1.1. Baseline Characteristics of Patient Population

CLAD is a heterogeneous disorder that may develop through different clinical phenotypes (1-4). Among the 50% of patients developing a CLAD by 5 years post-TP, 15% are restrictive allograft syndrome (RAS) and 35% are BOS (32). We focused on BOS, the most common (Table 1). Two groups of LT recipients were included in the study: 20 stable patients (STA) and 21 patients developing a BOS (BOS) in the 4 years post-TP. 20 healthy volunteers (HV) were added as controls. BOS is defined as patients with a decrease in lung function indicator FEV1 of at least 20% compared to maximum values assessed after transplantation and an airway-fibrosis exclusively obstructive disease. None of the usual risk factors of CLAD significantly differed between STA and BOS patients. Indeed, most of the patients received bilateral lung transplantation (67% and 63% of STA and BOS respectively). Recipient age (mean of 48 and 59 years for STA and BOS respectively), immunosuppressive treatments, ischemic time, number of acute cellular rejection events, infections, CMV, EBV and HLA mismatches and DSA at transplantation were not significantly different between BOS and STA. Concerning the initial disease leading to lung transplantation, the number of Cystic Fibrosis (CF) patients was higher in the STA (50% vs 14% respectively) which is representative of the COLT cohort. All the baseline characteristics are provided in Table 1.

1.2. $CD24^{hi}CD38^{hi}$ Transitional B Cell Rate 24 Month Post-LT.

Figure 1B:
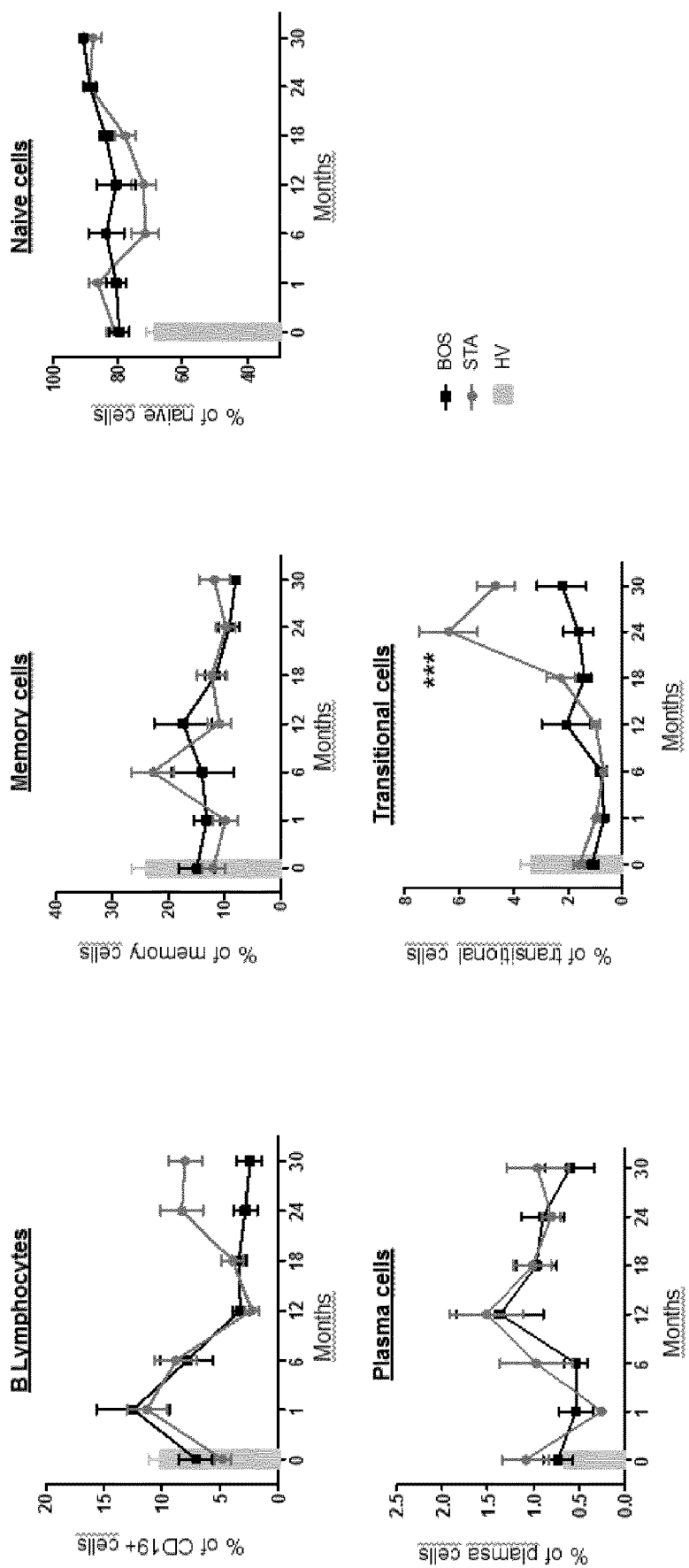
Figure 1C:
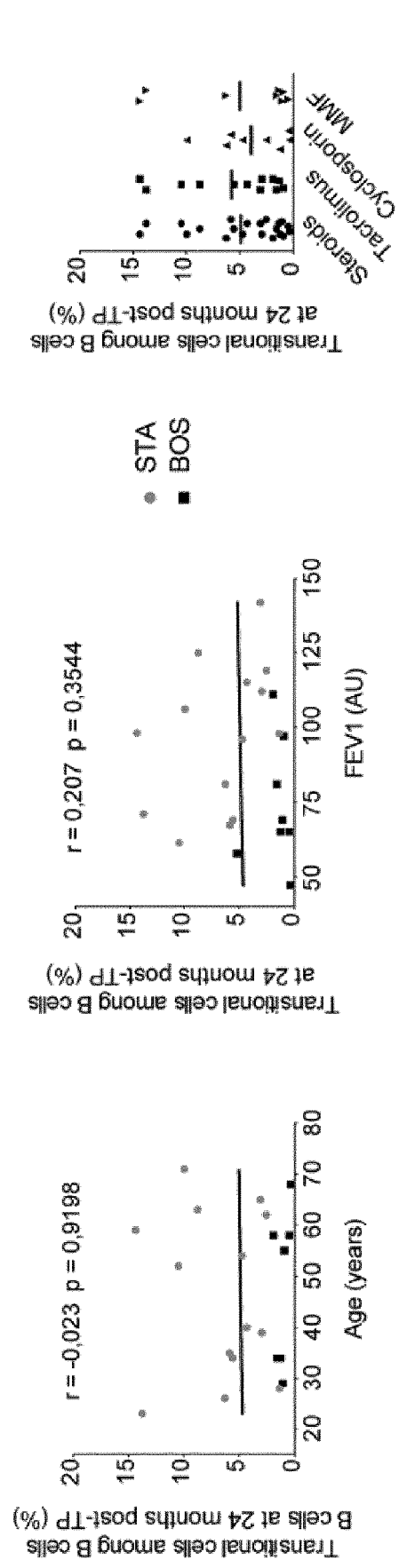

Because B cells homeostasis is reshaped in the context of allograft chronic dysfunction (40, 41) we assess whether peripheral blood B-lymphocytes subset profiles may evolve differently in time between BOS, STA (from inclusion, before LT to 30 months post-LT) and HV. Results from BOS patients at the time of diagnosis and after were excluded (supplementary data 1), then all the patients in the following analysis display normal graft function at the different time points. Based on the expression of CD19, CD27, CD38, CD22 and CD24, we determined the percentage of naive, memory, transitional B cells and plasma cells (FIG. 1A). Total CD19+ B cells was not different between BOS, STA and HV at any time points (FIG. 1B). No significant difference was observed for any B cell subtypes either, except for the $CD24^{hi}CD38^{hi}$ transitional B cells that stayed low during time in BOS patients (1.1%±0.1) whereas increasing in patients with a stable graft function to reach a maximum peak at 24 month (6.3%±0.1; p≤0.001), with a level of $CD24^{hi}CD38^{hi}$ transitional B cells superior to HV (3.3%±0.4; p≤0.01). This increase in $CD24^{hi}CD38^{hi}$ transitional B cells is not associated with age nor pulmonary lung capacity of the patients (FIG. 1C).

1.3. IL10 Producing $CD24^{hi}CD38^{hi}$ Transitional B Cells and CD9+ B Cell Frequencies Discriminate BOS and STA at 24 Months.

Figure 2A:
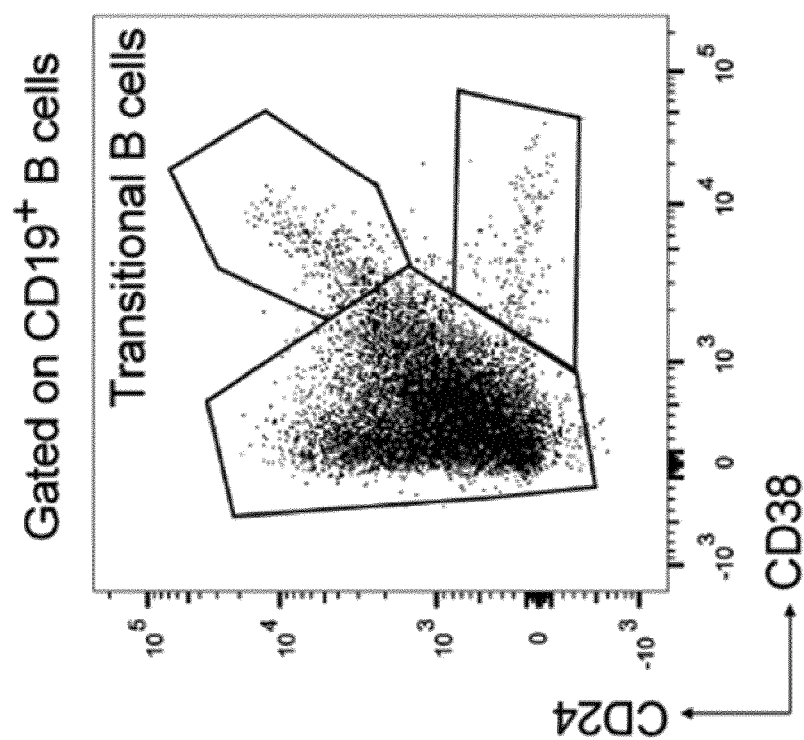
FIG. 2: Longitudinal immunomonitoring of transitional B cell subtypes during time. A) Gating strategy of CD19$^+$ CD24$^{hi}$CD38$^{hi}$ transitional cells, CD27$^-$IgD$^{+/low}$IgM$^+$ T1/2, CD27$^-$Igd$^+$IgM$^-$ T3, CD27$^+$ non-conventional memory transitional B cells. B) Longitudinal immuno monitoring of T1/T2, T3, CD27$^-$ non-conventional and CD19$^+$ CD24$^{hi}$CD38$^{hi}$CD9$^+$ B cells before LT, 1, 6, 12, 18, 24 and 30 months post-LT in STA (n=20), BOS (n=21) and HV (n=20) patients. C) Longitudinal immunomonitoring of CD9$^+$ B cells before LT, 1, 6, 12, 18, 24 and 30 months post-LT in STA, BOS and HV patients.
Figure 2B:
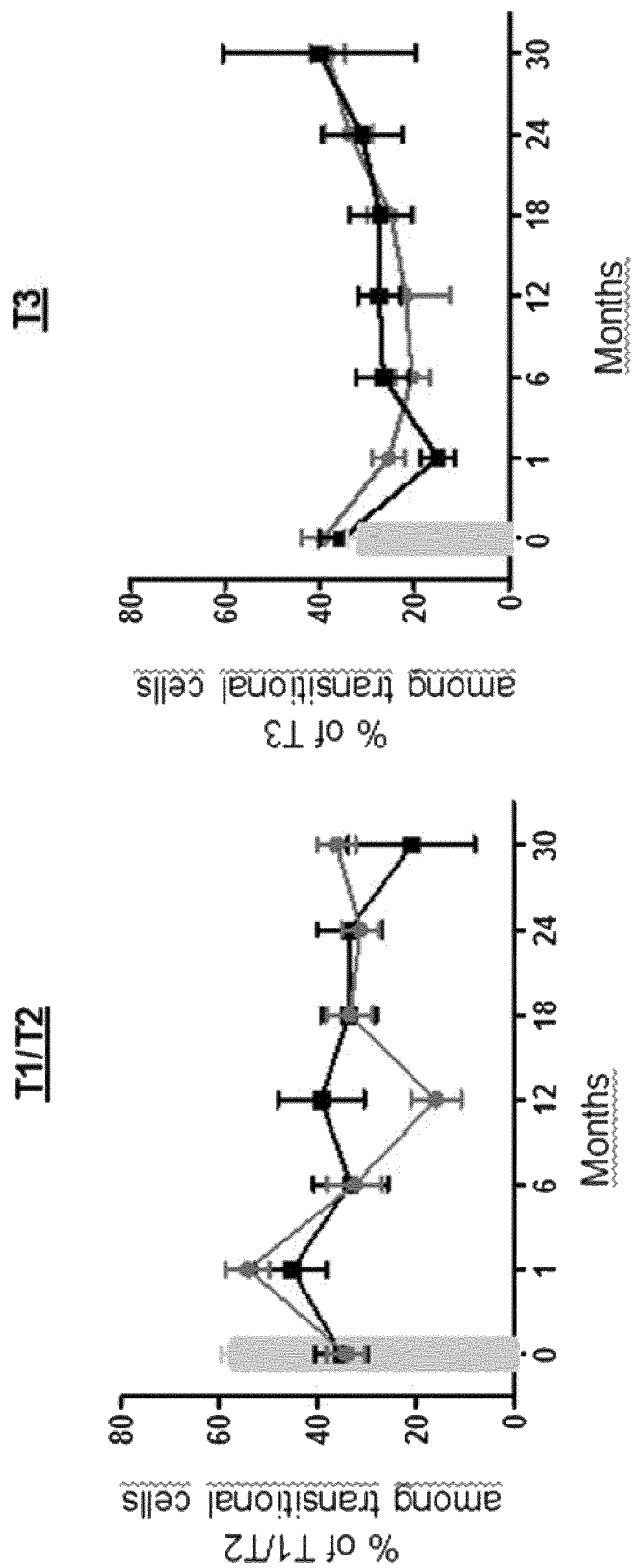
Figure 2C:
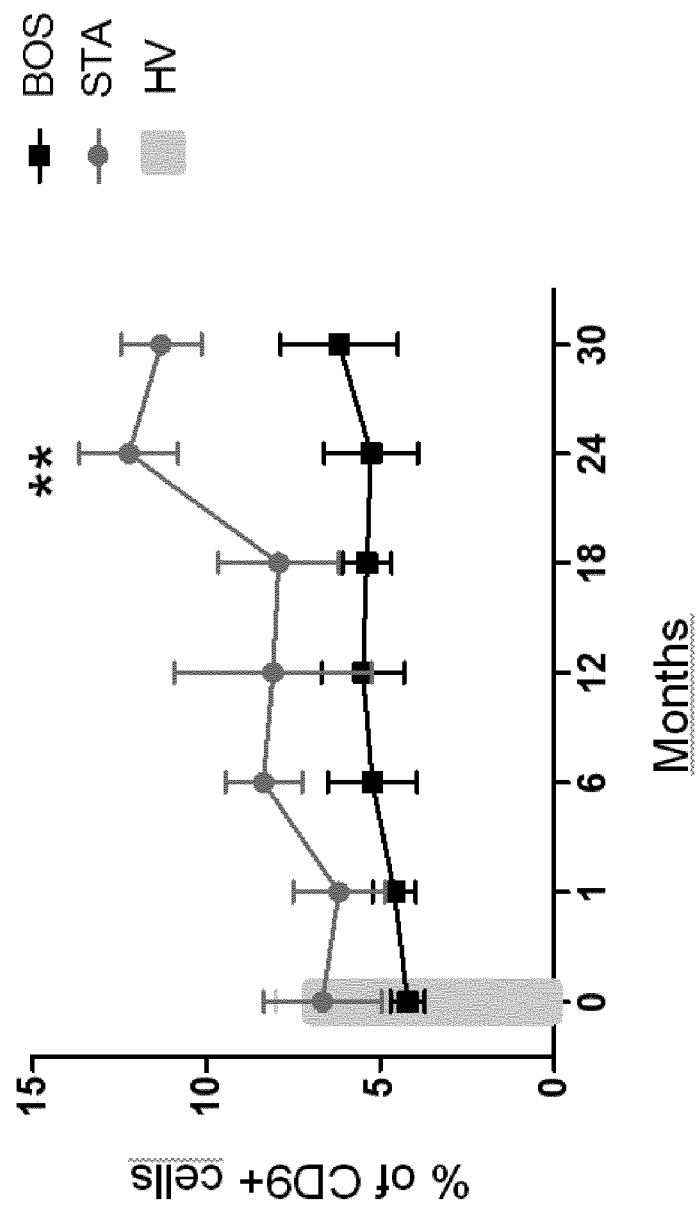

We analysed the frequency of $CD24^{hi}CD38^{hi}$ sub-populations in STA, BOS and HV, depending on their differentiation states and CD9 markers associated in the literature with regulation. CD9, CD27, IgM and IgD surface markers were used to distinguish $CD24^{hi}CD38^{hi}$ transitional B-cell subsets: $CD27^-IgD^{+/low}IgM^+$ T1/2, $CD27^-IgD^+IgM^-$ T3, $CD27^+$ non-conventional memory transitional B cells and $CD9^+$ $CD24^{hi}CD38^{hi}$ transitional B-cells (FIG. 2A). The frequency of transitional B cell subset was not different within groups at any time point (FIG. 2B). We observe a significant peak of all $CD24^{hi}CD38^{hi}$ transitional B cell subsets at 24 months post-LT in STA patients whereas remaining low in BOS: T1/T2 (2.5%±0.5 vs 0.5±0.1 in STA and BOS, p≤0.001), T3 (2.6%±0.6 vs 0.8±0.5 in STA and BOS, p<0.005), CD27+ non-conventional B cells (0.5%±0.07 vs 0.15±0.06 in STA and BOS, p<0.001) and $CD9^+$ $CD24^{hi}CD38^{hi}$ transitional B-cells (2.8%±0.5 vs 0.6±0.3 in STA and BOS, p<0.001). Interestingly, CD9+ B cell frequency alone is significantly higher at 24 months post-LT in STA compared to BOS (12.2%±1.1 vs 5.2±1 respectively at 24 month post-LT, p≤0.005) (FIG. 2C).

Figure 3A:
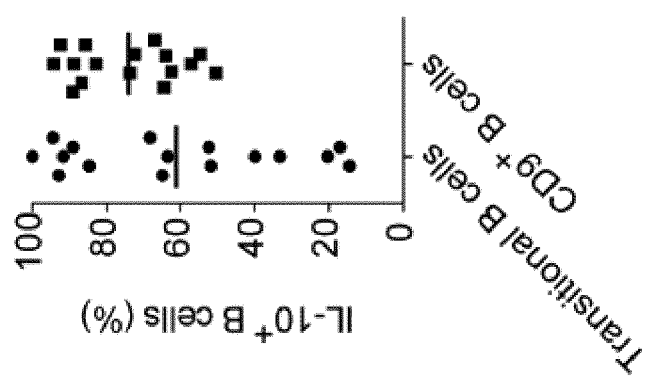
FIG. 3A illustrates the percentage of transitional and CD9+ B cells secreting IL-10 in LT recipients.
Figure 3B:
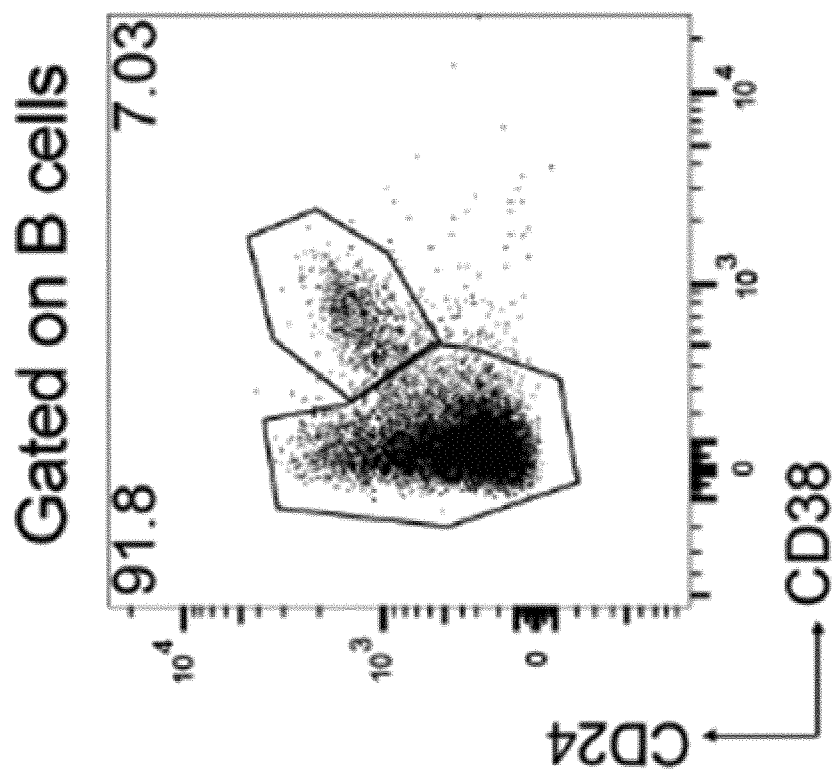
FIG. 3B: illustrates a representative staining of IL-10+ B cells in CD19$^+$ CD24$^{hi}$CD38$^{hi}$ transitional, non transitional, CD9+, and CD9− B cells.
Figure 3B:
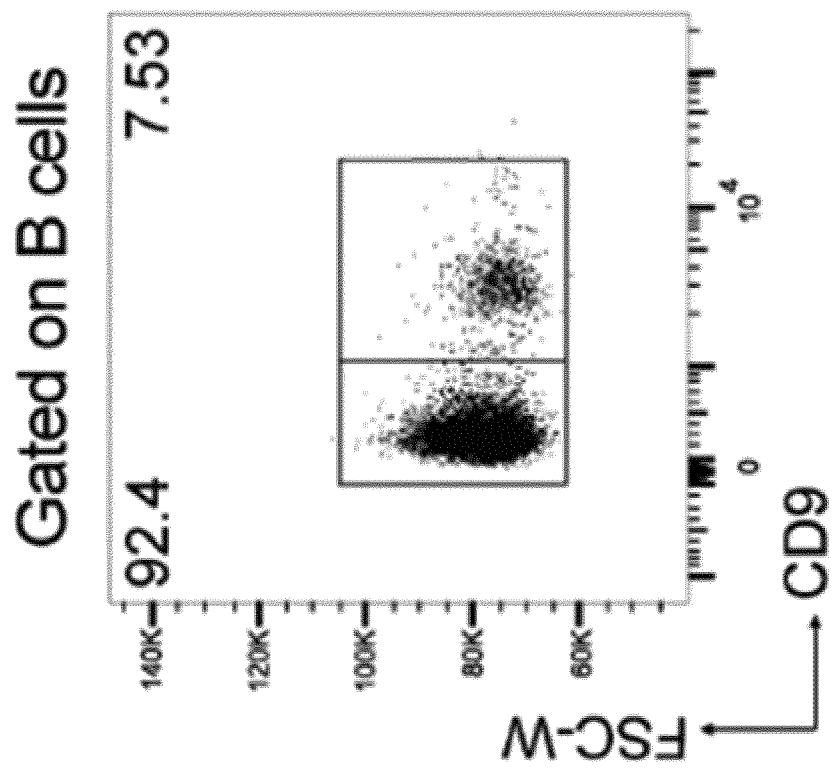

We analyzed IL-10 production by transitional and CD9+ B cells in vitro after activation with PMA and ionomycin in LT recipients. Both transitional and CD9+ B cells are able to secrete substantial IL-10 (61.2%±6.9 and 70.7%±3.7 respectively) (FIG. 3A, 3B). Altogether, these data show that IL-10 secreting $CD24^{hi}CD38^{hi}$ transitional B cells and/or CD9+ B cells discriminate BOS and STA 24 months after LT.

1.4. $CD9^+$ B Cell is a Predictive Marker of Long-Term BOS-Free Survival at 24 Months Post-LT.

Figure 4A:
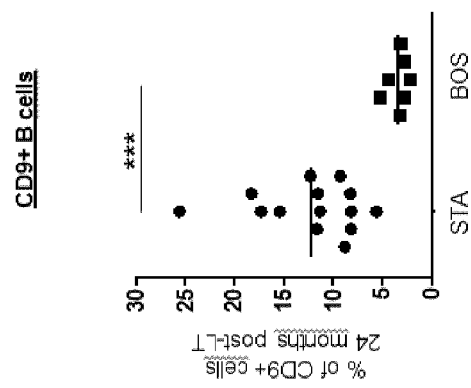
FIG. 4: Correlation between CD19+CD24hiCD38hi transitional cells or CD9+ level at 24 months and BOS incidence. A) Percentage of transitional and CD9+ B cells 24 months post-LT in STA and BOS patients. B) ROC curve (upper part of FIG. 4) and Kaplan-Meier analysis (lower part of FIG. 4) of the level of transitional and CD9+ B cells 24 months post-LT in BOS and STA patients (AUC=0.98, SE=0.02, cut-off=2.24 at 100% sensitivity and 92.8% specificity and AUC=1, SE=0, cut-off=5.4 at 100% sensitivity and 100% specificity; respectively).
Figure 4A:
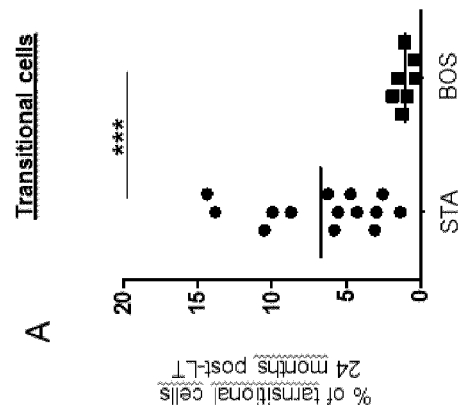

We next investigated whether the level $CD19^+$ $CD24^{hi}CD38^{hi}$ transitional cells and/or $CD9^+$ B cells would be sufficient to discriminate between patients who will maintain stable graft function and those who will develop a BOS in the 5 years after LT. We report on a highly significant difference in CD9 expression between STA and BOS groups at 24 months post-LT (p<0.001) (FIG. 4A).

Figure 4B:
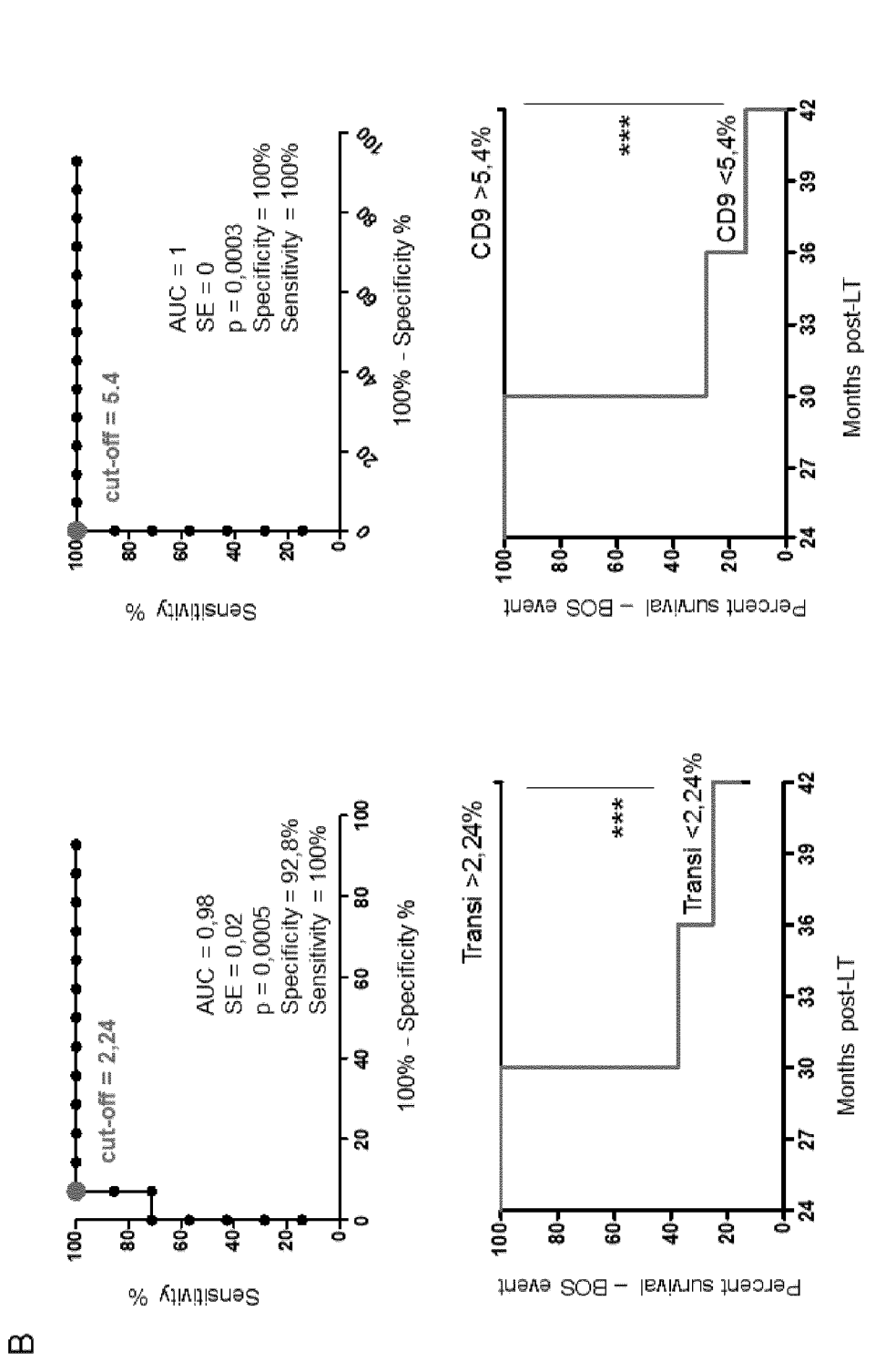

We determined the best cut-off of ROC curves, 2.24% for transitional B cells (sensitivity=100%, specificity=93%) and 5.4% for CD9+ B cells (sensitivity and specificity of 100%). Patients with CD9+ or transitional B cell frequency below these cut-off points displayed significantly higher incidence of BOS (log-rank p=0.001) (FIG. 4B). Together these data show that an increase of circulating transitional B cells and/or CD9+ B cells 24 months post-LT predict long-term BOS-free survival.

According to the ROC curve analysis, the rate of 2.24% transitional B cells and 5.4% $CD9^+$ B cells allow to discriminate STA and BOS patients at 24 months post-LT (AUC=0.98, SE=0.02, cut-off=2.24 at 100% sensitivity and 92.8% specificity and AUC=1, SE=0, cut-off=5.4 at 100% sensitivity and 100% specificity; respectively). Similarly, patients with $CD9^+$ or transitional B cell frequency below 5.4% and 2.24% respectively at 24 months (Log-rank p=0.001) displayed significantly higher incidence of BOS (Log-rank p=0.05) (FIG. 4B). These results show that both the level of $CD19^+$ $CD24^{hi}CD38^{hi}$ transitional and $CD19^+$ $CD9^+$ B cells are directly associated with graft outcome. An increase of circulating transitional B cells and/or CD9+ B cells 24 months post-LT predict long-term BOS-free survival. $CD9^+$ B cell level is nonetheless more powerful as predictive biomarker of BOS than transitional cells with AUC=1, 100% sensitivity and 100% specificity.

1.5. A 1% CD9+ 1-24 Month Ratio Determine BOS Event.

In order to propose CD9+ as a biomarker of BOS and its use in routine in lung transplantation, we focus on the CD9+ 1-24 month fold change level. We calculated the ratio of the rate of CD9+ B cells at one month over 24 in the 21 BOS and 20 STA patients included in this study.

Figure 5:
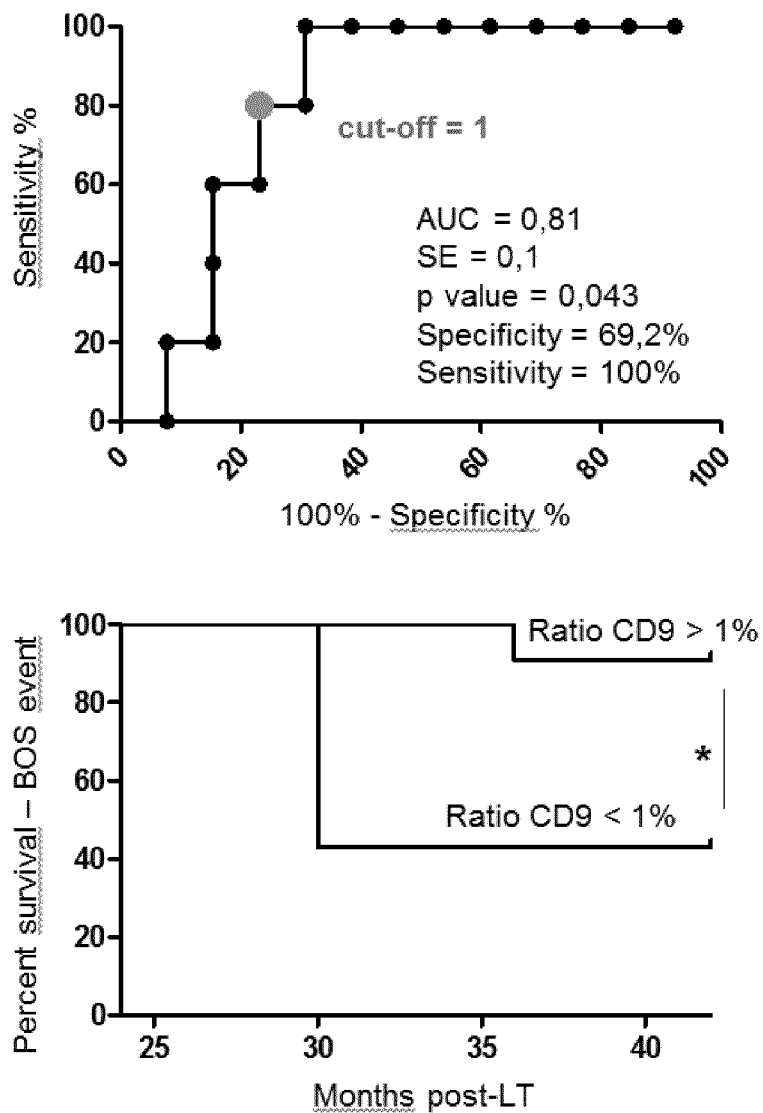
FIG. 5: CD9+ B cell is a predictive marker of long-term BOS-free survival at 24 months post-LT.: ROC curve (upper part of FIG. 5) and:Kaplan-Meier analysis (lower part of FIG. 5) of the CD9+1-24 month fold change level in BOS and STA patients (AUC=0.81, SE=0.1, cut-off=1 at 100% sensitivity and 69.2% specificity).
Figure 6:
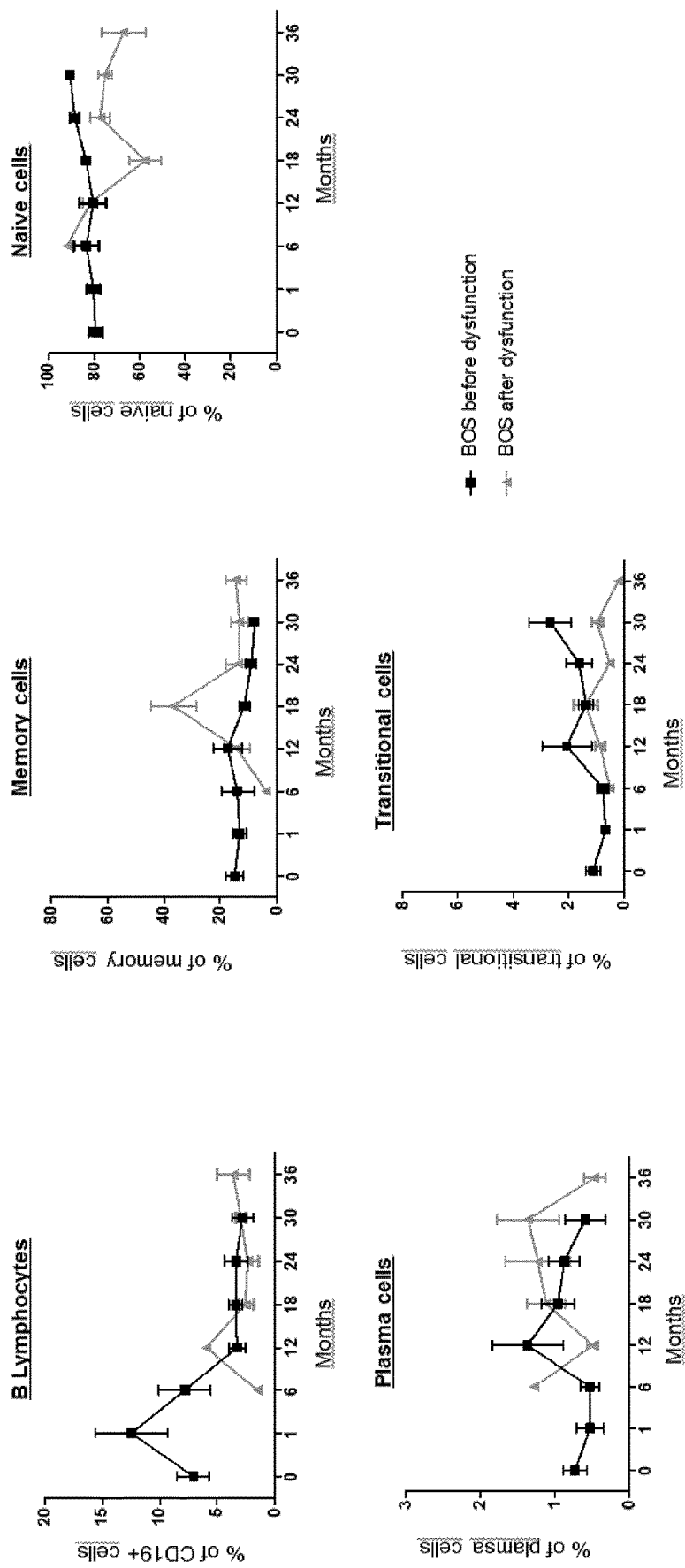
FIG. 6: Longitudinal immunomonitoring of B lymphocyte subpopulations during time in BOS patients. Longitudinal immunomonitoring of CD19+ B cells, transitional, memory, naïve and plasma cells before LT, 1, 6, 12, 18, 24 and 30 months post-LT in BOS patients (n=21) before (black) or after (grey) lung dysfunction.

We first performed ROC curve analysis to determine the cut-off allowing the best discrimination between the two groups (FIG. 5A). We reported that patients with a fold change of $CD9^+$ B cells at 24/1 month above 1% allow the discrimination between BOS and STA lung transplanted patient (AUC=0.81, SE=0.1, cut-off=1 at 100% sensitivity and 69.2% specificity). Based on these data, the Kaplan-Meier analysis show that patients with a fold change of $CD9^+$ B cells at 24/1 month above 1 displayed significantly higher BOS-free survival (Log-rank p=0.05) (FIG. 5B) and the high AUC highlight the strong prediction. Altogether these data show that a 1% CD9+ 1-24 month ratio determine BOS event, which also mean that an increase of CD9+ anytime post-LT is predictive of long-term BOS-free survival.

1.6. Discussion of the Results

The understanding of cellular and molecular mechanisms of graft failure and the identification of robust predictive biomarkers for allograft outcome steel the major challenges facing clinicians involved in lung transplantation. Although numerous studies interested in the factors associated with Bronchiolitis Obliterans Syndrome (BOS) occurrence, the overall mechanisms comprehension needed to manage long-term rejection remains unclear. Most of the investigations interested in the role of allograft recipient immunity but omit the potential role of B cells, except in the donor specific antibodies (DSA) secretion. However, it is now well recognized that B lymphocytes play a complex role, being able to produce cytokines (45), to express costimulatory molecules (46) and to present antigens (47). They are thus capable of both promoting and regulating inflammation. This study report for the first time the longitudinal homeostasis modifications of circulating B cell subsets in lung transplant recipients presenting stable graft functions or developing BOS. We thus report that stable lung transplant recipients harbor an increase of $CD24^{hi}CD38^{hi}$ transitional B cells 24 months post-LT while it stays low in BOS patients and that CD9+ that characterize $CD24^{hi}CD38^{hi}$ transitional B cells may serve as biomarker of BOS.

BOS is a strictly clinical definition using pulmonary function testing allowing the diagnosis of CLAD. It is defined as a persistent decrease in FEV1 of at least 20% compared with the mean of the two best postoperative values in the absence of any other identifiable cause (4). Although significant progress has been made, the exact pathophysiological mechanisms remain unknown and this multifactorial disease remains irreversible and unpredictable so far. It seems now clear that both innate and adaptive immune response induced by the allograft itself or by the environment may lead to allograft dysfunction (1). And now, it is well established that the role of B lymphocyte is overriding.

We clearly reported in a model of operational tolerance in human, a significant increase in frequency of total B cells, particularly activated, memory and early memory B cells with a significantly enriched transcriptional B-cell profile (17). Newell and colleagues described a B cell gene signatures distinguishing tolerant patients and identifies 3 genes that predict tolerance (IGKV4-1, IGLL1, and IGKV1D-13) (19). This signature was associated with elevated numbers of peripheral blood, naïve and transitional B cells in tolerant participants compared with those receiving immunosuppression. High level of CD24$^{hi}$CD38$^{hi}$ transitional B cells has also been reported in kidney, skin (20) and allogeneic hematopoietic stem cell transplantation (14), as being associated with better graft survival. Some studies showed that tolerance was associated with the increased frequencies of transitional and naïve B cells suggesting that a shift towards a naïve/transitional B-cell phenotype might be a prerequisite for the development of tolerance (25, 13, 17). Shabir and al. also confirmed that transitional B cells were associated with protection from kidney graft rejection (20). Conversely, a decrease of circulating transitional cells correlated with the incidence of graft rejection events (26).

In the last decade, transitional B cells had gained attention due to their regulatory activity, mainly based on anti-inflammatory cytokine IL-10 secretion (28). We observed that the frequency of IL-10 secreting B-cells was significantly higher in STA patients compared to BOS (data not shown) and that IL-10-secreting cells were mainly enriched in the transitional subset. We have previously identified the CD9 as a marker of CD24$^{hi}$CD38$^{hi}$ transitional cells with regulatory properties (23). We report here for the first time in lung, that the rate of transitional cells and CD9 are associated with long-term BOS-free survival. Among these transitional B cells, Simon and colleagues provided new evidence for the existence of four subsets with distinct phenotypes and regulatory properties. T1 cells, with an immature differentiation pattern are CD24$^{hi}$CD38$^{high}$CD27$^-$IgD$^{hi}$IgM$^+$; T2 cells, showing growing maturity markers expression are CD24$^{hi}$CD38$^{hi}$CD27$^-$IgD$^+$IgM$^-$; T3 cells phenotypically near to mature B cells are CD24$^{hi}$CD38$^{hig}$CD27$^-$IgD$^-$IgM$^+$ and memory-like transitional B cells are CD24$^{hi}$CD38$^{hi}$CD27$^+$. We followed Simon's description to defined T1/2, T3 and CD27$^+$ transitional subtypes based on IgM, IgD and CD27 expression. In our study, all transitional subsets proportions among B cells were increased in STA compared to BOS patients 24 months post-LT. Moreover, this increase of transitional B cells in STA reach a pick over the level of HV. Interestingly this extra-physiological raise have been observed in some protocols of induction therapy in renal transplantation. Alemtuzumab induction therapy was shown to deplete effectively B cells, but is was followed by rapid repopulation of transitional and naïve B cells up to levels exceeding base line, creating an environment in which tolerance may be achieved (44). These results strengthened our similar data suggesting that transitional rate is associated with long term graft outcome.

As mentioned above, several studies have been carried out to identify early indicators of CLAD in order to improve long-term lung allograft survival. In lung allograft biopsies collected within the first year post-LT, integrating the mRNA expression levels of five genes from the transforming growth factor-☐ axis into a score, patient groups can be confidently separated and the outcome predicted (5). Also significantly elevated percentages of BAL neutrophils and IL-8 level and upregulation of RANTES and MCP-1 were found between 4 and 10 months before BOS diagnosis (6.7).

It was also shown that the pro-inflammatory cytokine response following transplantation was associated with a trend towards development of BOS, more specifically, an elevation in circulating IL6, 24 h post-LT (8). Another study focused on Endothelin-1, a potent mitogenic and profibrotic peptide produced by pulmonary vascular endothelial cells that play a role in the pathophysiology of CLAD (9). They found that before LT, 3 and 12 months post-LT, Endothelin-1 serum concentration was significantly higher in patient who will develop BOS. Also, the pre-LT and 3 month post-LT Endothelin-1 level was predictive for BOS and at 12 month post-LT, it was diagnostic for BOS. sCD59 is a protein present in various body fluids and is associated with cellular damage after acute myocardial infarction. Budding and colleagues demonstrated that LT patients with sCD59 titers ≥400 pg/ml 6 months post-LT had a significant lower chance of BOS-free survival than patients with titers ≤400 pg/ml. Human leukocyte antigen G (HLA-G) expression was thought to be associated with a tolerance state following solid organ transplantation. Brugière et al., aimed to confirm the prognostic value of HLA-G expression in the graft and plasma to identify LT recipients with low immunologic risk of chronic rejection. They found that within the first year post-LT, HLA-G expression in the lung was associated with graft acceptance in the long term. Finally, we revealed a rise in plasma MMP-9 before CLAD onset and MMP-9 concentration was predictive of the occurrence of CLAD 12 months before the functional diagnosis (47).

Despite the different studies already performed, none have demonstrated enough robustness to achieve clinical acceptance, having several limitations. Concerning the study on IL-6, a trend between IL-6 rising and the development of BOS and acute rejection was found such as a significant association between IL-6 elevation and survival. Because viral infections are known to induce HLA-G expression, this issue highly limits the clinical usefulness of graft HLA-G expression in real-life practice during follow-up of transplanted patents. Also, the plasma sHLA-G level, which could serve as a potential noninvasive marker, was not associated with graft outcome. The main limitation of all these studies is the small sample size which limits the inclusion of covariates in the analysis. Hence, biomarkers described in these studies have to be validated in a larger and multicenter cohort.

In this paper, since CD24$^{hi}$CD38$^{hi}$ transitional B cells is largely increased in STA and lacking in BOS 24 month post-LT, we asked whether transitional cells and CD9 associated markers may be correlated with graft outcome in LT. We showed that the monitoring of CD24$^{hi}$CD38$^{hi}$ transitional B cells or CD9+ B cells could serve as biomarker to risk-stratify patients 24 months post-LT. Indeed, absolute proportion of CD9$^+$ B cells (>5.4% among B cells, 24 months after TP) and transitional B cells (>2.24% among B cells, 24 month after TP), allow distinction between patients who will develop a BOS and LT recipients with a long-term stable graft function. However, we are convinced that the use of extracellular regulatory markers CD9 expression on total circulating CD19$^+$ B cells would be more appropriate for clinical use. In the same way to be use in routine, the analysis of the fold change between 1 month and 24 months post-TP for CD9$^+$ would be tougher excluding individual variability. Hence, we report that patients with low risk of BOS development are significantly determined by an increase of CD9+ B cells anytime post-TP compared to 1-month post-LT rate.

Here the CD9 marker is very robust but our study has also limitations. Although we worked with a reasonable number of patients, CD9 marker have to be validated on an independent cohort of LT recipients in a prospective follow-up. Also CD9 alone may be insufficient for prediction of CLAD and combining several markers, could be an adjunct tool to risk-stratify patients.

In the literature, transitional B cells homeostasis modification has been associated with different treatments. In lung recipients, it was shown that both anti-calcineurin and mTOR inhibitor treatments reduced regulatory B cell populations (35, 36) and that recipient under tacrolimus exhibit a decrease of $CD24^{hi}CD38^{hi}B$ cells (37). On the other hand, Leibler and colleagues have shown that Belatacept influences B cell compartment by favoring the occurrence of transitional B cells with regulatory properties (38). Doubtless, more studies have to be performed to determine if treatments administration could be improved taking their effects on transitional B cells into account.

In summary, these data are the first to reveal that $CD24^{hi}CD38^{hi}$ transitional B cells are associated with better lung allograft outcome. They may act as key actors in creating a favorable environment in which regulation of inflammation may be achieved and might be essential for the maintenance of long-term stable graft function after lung transplantation. Finally, the entirely new identification of CD9 expressing B-cells as predictive biomarkers of long-term BOS free survival may allow to lighten or straighten treatments according to its circulating level. These data could help early prediction of BOS and development of personalized medicine, a major breakthrough, based on risk stratification and personalized pathways modulation.

TABLE 1

|  | Stable | BOS | p-value |
|---|---|---|---|
| Number of patients | 20 | 21 |  |
| Median occurrence of CLAD (month after Tx) [range] |  | 24 [12-42] |  |
| Median Age at Tx [range] | 48 [23-71] | 59 [27-68] | 0.583 |
| Sex, n (%) |  |  |  |
| Male | 8 (40) | 10 (48) | 0.285 |
| Female | 12 (60) | 11 (52) |  |
| Median Donor age [range] | 49 [18-71] | 44 [16-65] | 0.937 |
| Sex, n (%) |  |  |  |
| Male | 10 (50) | 12 (57) | 0.661 |
| Female | 10 (50) | 9 (43) |  |
| Pathology leading to Tx, n (%) |  |  |  |
| Emphysema/COPD | 7 (35) | 9 (43) | 0.708 |
| CF | 10 (50) | 3 (14) | 0.012 |
| PAH | 2 (10) | 6 (29) | 0.143 |
| IPF | 1 (5) | 2 (9) | 0.542 |
| Other | 0 | 1 (5) | 0.584 |
| Type of Tx, n(%) |  |  |  |
| double lung | 15 (75) | 14 (67) | 0.64 |
| single lung | 5 (25) | 6 (28) | 0.439 |
| Lobar | 0 | 1 (5) | 0.584 |
| Median Inschemic time (min) [range] | 315 [215-467] | 330 [150-540] | 0.648 |
| Induction, n(%) |  |  |  |
| Basiliximab | 9 (45) | 5 (24) | 0.16 |
| Thymoglobulin | 8 (40) | 12 (57) | 0.158 |
| None | 3 (15) | 4 (19) | 0.642 |

TABLE 1-continued

|  | Stable | BOS | p-value |
|---|---|---|---|
| Immunosuppressives, n(%) |  |  |  |
| Steroids | 18 (90) | 18 (86) | 0.695 |
| Tacrolimus | 12 (60) | 8 (38) | 0.285 |
| Cyclosporin | 7 (35) | 12 (58) | 0.164 |
| MMF | 7 (35) | 11 (52) | 0.161 |
| Acute cellular rejections, n(%) |  |  |  |
| Ever A1 grade | 8 (40) | 9 (43) | 0.96 |
| Ever ≥A2 grade | 7 (35) | 4 (19) | 0.23 |
| Infections, n(%) |  |  |  |
| Bacteria | 15 (75) | 18 (89) | 0.607 |
| Virus | 14 (70) | 16 (73) | 0.859 |
| Fungi | 14 (70) | 10 (42) | 0.116 |
| Mismatch |  |  |  |
| CMV, n(%) | 10 (50) | 9 (43) | 0.661 |
| Toxoplasmosis, n(%) | 7 (35) | 7 (37) | 0.841 |
| EBV, n(%) | 2 (10) | 2 (9) | 0.978 |
| HLA (average score/8) | 5 (25) | 5 (24) | 0.081 |
| DSA at Tx | 5 (25) | 7 (37) | 0.348 |

REFERENCES

1. Royer P J, Olivera-Botello G, Koutsokera A, Aubert J D, Bernasconi E, Tissot A, Pison C, Nicod L, Boissel J P, Magnan A; SysCLAD consortium. Chronic Lung Allograft Dysfunction: A Systematic Review of Mechanisms. *Transplantation* 2016; 100:1803-14.
2. Yusen R D, Edwards L B, Kucheryavaya A Y, Benden C, Dipchand A I, Dobbels F, Goldfarb S B, Lewey B J, Lund L H, Meiser B, Stehlik J; International Society for Heart and Lung Transplantation. The registry of the International Society for Heart and Lung Transplantation: thirty-first adult lung and heart-lung transplant report—2014; focus theme: retransplantation. *J Heart Lung Transplant* 2014; 33:1009-24.
3. Barker AF1, Bergeron A, Rom W N, Hertz M I. Obliterative bronchiolitis. *N Engl J Med* 2014; 370:1820-8.
4. Verleden S E, Sacreas A, Vos R, Vanaudenaerde B M, Verleden G M. Advances in Understanding Bronchiolitis Obliterans After Lung Transplantation. *Chest* 2016; 150: 219-25.
5. Jonigk D, Izykowski N, Rische J, Braubach P, Kiihnel M, Warnecke G, Lippmann T, Kreipe H, Haverich A, Welte T, Gottlieb J, Laenger F. Molecular Profiling in Lung Biopsies of Human Pulmonary Allografts to Predict Chronic Lung Allograft Dysfunction. *Am J Pathol* 2015; 185:3178-88.
6. Neurohr C, Huppmann P, Samweber B, Leuschner S, Zimmermann G, Leuchte H, Baumgartner R, Hatz R, Frey L, Ueberfuhr P, Bittmann I, Behr J; Munich Lung Transplant Group. Prognostic value of bronchoalveolar lavage neutrophilia in stable lung transplant recipients. *J Heart Lung Transplant* 2009; 28:468-74.
7. Reynaud-Gaubert M, Marin V, Thirion X, Farnarier C, Thomas P, Badier M, Bongrand P, Giudicelli R, Fuentes P. Upregulation of chemokines in bronchoalveolar lavage fluid as a predictive marker of post-transplant airway obliteration. *J Heart Lung Transplant* 2002; 21:721-30.
8. Hall D J, Baz M, Daniels M J, Staples E D, Klodell C T, Moldawer L L, Beaver T M. Immediate postoperative inflammatory response predicts long-term outcome in lung-transplant recipients. *Interact Cardiovasc Thorac Surg* 2012; 15:603-7.

9. Salama M, Jaksch P, Andrukhova O, Taghavi S, Klepetko W, Aharinejad S. Endothelin-1 is a useful biomarker for early detection of bronchiolitis obliterans in lung transplant recipients. *J Thorac Cardiovasc Surg* 2010; 140: 1422-7.
10. Budding K, van de Graaf E A, Kardol-Hoefhagel T, Kwakkel-van Erp J M, Luijk B D, Oudijk E J, van Kessel D A, Grutters J C, Hack C E, Otten H G. Soluble CD59 is a Novel Biomarker for the Prediction of Obstructive Chronic Lung Allograft Dysfunction After Lung Transplantation. *Sci Rep* 2016; 6:26274.
11. Brugière O, Thabut G, Krawice-Radanne I, Rizzo R, Dauriat G, Danel C, Suberbielle C, Mal H, Stern M, Schilte C, Pretolani M, Carosella E D, Rouas-Freiss N. Role of HLA-G as a predictive marker of low risk of chronic rejection in lung transplant recipients: a clinical prospective study. *Am J Transplant* 2015; 15:461-71.
12. Braza F, Durand M, Degauque N, Brouard S. Regulatory T Cells in Kidney Transplantation: New Directions? *Am J Transplant* 2015; 15:2288-300.
13. Moreau A, Blair P A, Chai J G, Ratnasothy K, Stolarczyk E, Alhabbab R, Rackham C L, Jones P M, Smyth L, Elgueta R, Howard J K, Lechler R I, Lombardi G. Transitional-2 B cells acquire regulatory function during tolerance induction and contribute to allograft survival. *Eur J Immunol.* 2015; 45:843-53.
14. Sarvaria A, Alsuliman A, Chew C, Sekine T, Cooper N, Mielke, de Lavallade H1, Muftuoglu M, Fernandez Curbelo I, Liu E, Muraro P A, Alousi A, Stringaris K, Parmar S2, Shah N, Shaim H, Yvon E, Molldrem J, Rouce R, Champlin R, McNiece I, Mauri C, Shpall E J, Rezvani K. Regulatory B cells are enriched within the IgM memory and transitional subsets in healthy donors but are deficient in chronic GVHD. *Blood.* 2014; 124:2034-45.
15. Chesneau M, Michel L, Dugast E, Chenouard A, Baron D, Pallier A, Durand J, Braza F, Guerif P, Laplaud D A, Soulillou J P, Giral M, Degauque N, Chiffoleau E, Brouard S. Tolerant Kidney Transplant Patients Produce B Cells with Regulatory Properties. *Am Soc Nephrol* 2015; 26:2588-98.
16. Zhao Y, Gillen J R, Meher A K, Burns J A, Kron I L, Lau C L. Rapamycin prevents bronchiolitis obliterans through increasing infiltration of regulatory B cells in a murine tracheal transplantation model. *J Thorac Cardiovasc Surg.* 2016; 151:487-96.e3.
17. Pallier A, Hillion S, Danger R, Giral M, Racapé M, Degauque N, Dugast E, Ashton-Chess J, Pettré S, Lozano J J, Bataille R, Devys A, Cesbron-Gautier A, Braudeau C, Larrose C, Soulillou J P, Brouard S. Patients with drug-free long-term graft function display increased numbers of peripheral B cells with a memory and inhibitory phenotype. *Kidney Int.* 2010; 78:503-13.
18. Sagoo P, Perucha E, Sawitzki B, Tomiuk S, Stephens D A, Miqueu P, Chapman S, Craciun L, Sergeant R, Brouard S, Rovis F, Jimenez E, Ballow A, Giral M, Rebollo-Mesa I, Le Moine A, Braudeau C, Hilton R, Gerstmayer B, Bourcier K, Sharif A, Krajewska M, Lord G M, Roberts I, Goldman M, Wood K J, Newell K, Seyfert-Margolis V, Warrens A N, Janssen U, Volk H D, Soulillou J P, Hernandez-Fuentes M P, Lechler R I. Development of a cross-platform biomarker signature to detect renal transplant tolerance in humans. *J Clin Invest.* 2010; 120:1848-61.
19. Newell K A, Asare A, Kirk A D, Gisler T D, Bourcier K, Suthanthiran M, Burlingham W J, Marks W H, Sanz I, Lechler R I, Hernandez-Fuentes M P, Turka L A, Seyfert-Margolis V L. Immune Tolerance Network ST507 Study Group. Identification of a B cell signature associated with renal transplant tolerance in humans. *J Clin Invest.* 2010; 120:1836-47.
20. Shabir S, Girdlestone J, Briggs D, Kaul B, Smith H, Daga S, Chand S, Jham S, Navarrete C, Harper L, Ball S, Borrows R. Transitional B lymphocytes are associated with protection from kidney allograft rejection: a prospective study. *Am J Transplant.* 2015; 15:1384-91.
21. Bouaziz J D, Yanaba K, Tedder T F. Regulatory B cells as inhibitors of immune responses and inflammation. *Immunol Rev.* 2008; 224:201-14.
22. Rosser E C, Mauri C. Regulatory B cells: origin, phenotype, and function. *Immunity.* 2015; 42:607-12.
23. Braza F, Chesne J, Durand M, Dirou S, Brosseau C, Mahay G, Cheminant M A, Magnan A, Brouard S. A regulatory CD9(+) B-cell subset inhibits HDM-induced allergic airway inflammation. *Allergy.* 2015; 70:1421-31.
24. Simon Q, Pers J O, Cornec D, Le Pottier L, Mageed R A, Hillion S. In-depth characterization of CD24(high) CD38(high) transitional human B cells reveals different regulatory profiles. *J Allergy Clin Immunol.* 2016; 137: 1577-1584.
25. Bigot J, Pilon C, Matignon M, Grondin C, Leibler C, Aissat A, Pirenne F, Cohen J L, Grimbert P. Transcriptomic Signature of the CD24hi CD38hi Transitional B Cells Associated With an Immunoregulatory Phenotype in Renal Transplant Recipients. *Am J Transplant.* 2016.
26. Svachova V, Sekerkova A, Hruba P, Tycova I, Rodova M, Cecrdlova E, Slatinska J, Honsova E, Striz I, Viklicky O. Dynamic changes of B-cell compartments in kidney transplantation: lack of transitional B cells is associated with allograft rejection. *Transpl Int.* 2016; 29:540-8.
27. Meyer K C, Raghu G, Verleden G M, Corris P A, Aurora P, Wilson K C, Brozek J, Glanville A R; ISHLT/ATS/ERS BOS Task Force Committee; ISHLT/ATS/ERS BOS Task Force Committee. An international ISHLT/ATS/ERS clinical practice guideline: diagnosis and management of bronchiolitis obliterans syndrome. *Eur Respir J.* 2014; 44:1479-503.
28. Blair P A, Noreña L Y, Flores-Borja F, Rawlings D J, Isenberg D A, Ehrenstein M R, Mauri C. CD19(b)CD24 (hi)CD38(hi) B cells exhibit regulatory capacity in healthy individuals but are functionally impaired in systemic Lupus Erythematosus patients. *Immunity.* 2010; 32:129-140.
29. Cherukuri A, Salama A D, Carter C R, Landsittel D, Arumugakani G, Clark B, Rothstein D M, Baker R J. Reduced human transitional B cell T1/T2 ratio is associated with subsequent deterioration in renal allograft function. *Kidney Int.* 2017; 91:183-195.
30. Burton H, Dorling A. Transitional B cell subsets-a convincing predictive biomarker for allograft loss? *Kidney Int.* 2017; 91:18-20.
31. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): a novel form of chronic lung allograft dysfunction. *J Heart Lung Transplant.* 2011; 30:735-42.
32. Verleden G M, Vanaudenaerde B M, Dupont L J, Van Raemdonck D E. Azithromycin reduces airway neutrophilia and interleukin-8 in patients with bronchiolitis obliterans syndrome. *Am J Respir Crit Care Med.* 2006; 174:566-70.
33. Verleden G M, Raghu G, Meyer K C, Glanville A R, Corris P. A new classification system for chronic lung allograft dysfunction. *J Heart Lung Transplant.* 2014; 33:127-33.

34. Tebbe B, Wilde B, Ye Z, Wang J, Wang X, Jian F, Dolff S, Schedlowski M, Hoyer P F, Kribben A, Witzke O, Hoerning A. Renal Transplant Recipients Treated with Calcineurin-Inhibitors Lack Circulating Immature Transitional CD19+CD24hiCD38hi Regulatory B-Lymphocytes. *PLoS One.* 2016; 11: e0153170.
35. Latorre I, Esteve-Sole A, Redondo D, Giest S, Argilaguet J, Alvarez S, Peligero C, Forstmann I, Crespo M, Pascual J, Meyerhans A. Calcineurin and mTOR inhibitors have opposing effects on regulatory T cells while reducing regulatory B cell populations in kidney transplant recipients. *Transpl Immunol.* 2016; 35:1-6.
36. Chung B H, Kim K W, Yu J H, Kim B M, Choi B S, Park C W, Kim Y S, Cho M L, Yang C W. Decrease of immature B cell and interleukin-10 during early-post-transplant period in renal transplant recipients under tacrolimus based immunosuppression. *Transpl Immunol.* 2014; 30:159-67.
37. Leibler C, Matignon M, Pilon C, Montespan F, Bigot J, Lang P, Carosella E D, Cohen J, Rouas-Freiss N, Grimbert P, Menier C. Kidney transplant recipients treated with belatacept exhibit increased naïve and transitional B cells. *Am J Transplant.* 2014; 14:1173-82.
38. Benitez A, Weldon A J, Tatosyan L, Velkuru V, Lee S, Milford T A, Francis O L, Hsu S, Nazeri K, Casiano C M, Schneider R, Gonzalez J, Su R J, Baez I, Colburn K, Moldovan I, Payne K J. Differences in mouse and human nonmemory B cell pools. *J Immunol.* 2014; 15:4610-9.
39. de Masson A, Bouaziz J D, Le Buanec H, Robin M, O'Meara A, Parquet N, Rybojad M, Hau E, Monfort J B, Branchtein M, Michonneau D, Dessirier V, Sicre de Fontbrune F, Bergeron A, Itzykson R, Dhédin N, Bengoufa D, Peffault de Latour R, Xhaard A, Bagot M, Bensussan A, Socié G. CD24(hi)CD27+ and plasmablast-like regulatory B cells in human chronic graft-versus-host disease. *Blood.* 2015; 12; 125:1830-9.
40. Chesneau M, Pallier A, Braza F, Lacombe G, Le Gallou S, Baron D, Giral M, Danger R, Guerif P, Aubert-Wastiaux H, Néel A, Michel L, Laplaud D A, Degauque N, Soulillou J P, Tarte K, Brouard S. Unique B cell differentiation profile in tolerant kidney transplant patients. *Am J Transplant.* 2014:144-55.
41. Yanaba K, Bouaziz J D, Haas K M, Poe J C, Fujimoto M, Tedder T F. A regulatory B cell subset with a unique CD1dhiCD5+ phenotype controls T cell-dependent inflammatory responses. *Immunity.* 2008:639-50.
42. Sun J, Wang J, Pefanis E, Chao J, Rothschild G, Tachibana I, Chen J K, Ivanov I I, Rabadan R, Takeda Y, Basu U. Transcriptomics Identify CD9 as a Marker of Murine IL-10-Competent Regulatory B Cells. *Cell Rep.* 2015:1110-7.
43. Heidt S, Hester J, Shankar S, Friend P J, Wood K J. B cell repopulation after alemtuzumab induction-transient increase in transitional B cells and long-term dominance of naïve B cells. *Am J Transplant.* 2012; 12:1784-92.
44. Fillatreau S. Cytokine-producing B cells as regulators of pathogenic and protective immune responses. *Ann Rheum Dis.* 2013; 72 Suppl 2:ii80-4.
45. Crow M K. Costimulatory molecules and T-cell-B-cell interactions. *Rheum Dis Clin North Am.* 2004; 30:175-91.
46. Zanetti M, Castiglioni P, Rizzi M, Wheeler M, Gerloni M. B lymphocytes as antigen-presenting cell-based genetic vaccines. *Immunol Rev.* 2004; 199:264-78.
47. Pain M, Royer P J, Loy J, Girardeau A, Tissot A, Lacoste P, Roux A, Reynaud-Gaubert M, Kessler R, Mussot S, Dromer C, Brugière O, Mornex J F, Guillemain R, Dahan M, Knoop C, Botturi K, Pison C, Danger R, Brouard S, Magnan A; COLT Consortium. T Cells Promote Bronchial Epithelial Cell Secretion of Matrix Metalloproteinase-9 via a C-C Chemokine Receptor Type 2 Pathway: Implications for Chronic Lung Allograft Dysfunction. *Am J Transplant.* 2016; 10.1111.

The invention claimed is:

1. A method of preventing development of chronic lung graft dysfunction or treating chronic lung graft dysfunction in a lung transplant subject comprising:
   a) measuring the level of $CD9^+$ B cells in a blood sample of the lung transplant subject, and
   b) administering a preventive or therapeutic immunosuppressive treatment to the lung transplant subject when the level of $CD9^+$ B cells in the sample is lower than that of a reference value based on lung transplant subjects who did not reject a lung graft; wherein the amount of the immunosuppressive treatment prevents the development of chronic lung graft dysfunction or treats chronic lung graft dysfunction.

2. The method according to claim 1, wherein step a) is performed with a method further comprising measuring the level of $CD24^{hi}CD38^{hi}$ B cells from the blood sample of the lung transplant subject.

3. The method according to claim 2, wherein step a) is performed with a kit comprising one or more reagents for detecting or quantifying CD9 B cells in the blood sample of the lung transplant subject and further one or both of CD24 and CD38 B cells in the blood sample of the lung transplant subject.

4. The method according to claim 1, wherein step a) is performed with a kit comprising one or more reagents for detecting or quantifying CD9 B cells in the blood sample of the lung transplant subject.

* * * * *